United States Patent
Young

(10) Patent No.: US 9,326,722 B2
(45) Date of Patent: May 3, 2016

(54) METHODS OF PREDICTING AND MONITORING LABOR

(75) Inventor: Roger C. Young, Memphis, TN (US)

(73) Assignee: University of Vermont and State Agricultural College, Burlington, VT (US)

( * ) Notice: Subject to any disclaimer, the term of this patent is extended or adjusted under 35 U.S.C. 154(b) by 193 days.

(21) Appl. No.: 14/006,375

(22) PCT Filed: Mar. 21, 2012

(86) PCT No.: PCT/US2012/029939
§ 371 (c)(1),
(2), (4) Date: Oct. 22, 2013

(87) PCT Pub. No.: WO2012/129304
PCT Pub. Date: Sep. 27, 2012

(65) Prior Publication Data
US 2014/0039340 A1    Feb. 6, 2014

Related U.S. Application Data

(60) Provisional application No. 61/466,099, filed on Mar. 22, 2011.

(51) Int. Cl.
*A61B 5/00* (2006.01)
*A61B 5/0488* (2006.01)
*A61B 5/0492* (2006.01)

(52) U.S. Cl.
CPC .............. *A61B 5/4356* (2013.01); *A61B 5/0488* (2013.01); *A61B 5/0492* (2013.01)

(58) Field of Classification Search
CPC .............. A61B 5/033; A61B 5/0488–5/04882; A61B 5/0492; A61B 5/04012–5/04018; A61B 5/04; A61B 5/43; A61B 5/4306; A61B 5/4318–5/4356
USPC .......................................... 600/546, 588, 591
See application file for complete search history.

(56) References Cited

U.S. PATENT DOCUMENTS

| 5,297,549 A * | 3/1994 | Beatty et al. ................... 600/374 |
| 5,623,939 A * | 4/1997 | Garfield ......................... 600/546 |
| 2005/0159738 A1 * | 7/2005 | Visram et al. .................... 606/34 |
| 2007/0255184 A1 | 11/2007 | Shennib |

(Continued)

FOREIGN PATENT DOCUMENTS

| WO | 9531932 A1 | 11/1995 |
| WO | 2012129304 A9 | 9/2009 |

OTHER PUBLICATIONS

Hassan, M., et al., "Improving the Classification Rate of Labor vs. Normal Pregnancy Contractions by Using EHG Multichannel Recordings", Conference of the IEEE Eng Med Biol Soc, Sep. 2010, pp. 4642-4645.*

(Continued)

*Primary Examiner* — Devin Henson
*Assistant Examiner* — Audrey J Parker
(74) *Attorney, Agent, or Firm* — John D. Lanza; Foley & Lardner LLP

(57) ABSTRACT

The invention includes, in part, methods and apparatus for determining the status of labor in a pregnant subject. In some embodiments of the invention, organ-level uterine function is determined as a measure of the status of labor such as non-labor (e.g. false labor), latent phase labor, active phase labor, or post-delivery.

14 Claims, 12 Drawing Sheets

(56) References Cited

U.S. PATENT DOCUMENTS

| | | | |
|---|---|---|---|
| 2010/0004715 A1* | 1/2010 | Fahey | 607/48 |
| 2011/0270118 A1* | 11/2011 | Garfield et al. | 600/546 |
| 2013/0274580 A1* | 10/2013 | Madsen et al. | 600/365 |

OTHER PUBLICATIONS

Hassan, M., et al., "Interactions between Uterine EMG at Different Sites Investigated Using Wavelet Analysis: Comparison of Pregnancy and Labor Contractions", EURASIP Journal on Advances in Signal Processing, 2010, vol. 2010, Article ID 918012, doi: 10.1155/2010/918012, 9 pages.*

Basford, Jr., "The Law of Laplace and its Relevance to Contemporary Medicine and Rehabilitation", Arch Phys Med Rehabil, Aug. 2002, vol. 83, No. 8, pp. 1165-1170.

Chen, CJ, et al., "Activities of Uterine Muscles From Rats in Late Pregnancy", Proc Natl Sci Counc Repub China B, 1989, vol. 13, No. 1, pp. 42-46.

Csapo, A., "The Diagnostic Significance of the Intrauterine Pressure. I", Obstetrical and Gynecological Survey, 1970, vol. 25(5), pp. 403-435.

Csapo, A., "The Diagnostic Significance of the Intrauterine Pressure. II. Clinical considerations and trials", Obstetrical and Gynecological Survey, 1970, vol. 25, No. 6, pp. 515-543.

Csapo, A., et al., "Effect of Progesterone on the Electric Activity and Intrauterine Pressure of Pregnant and Parturient Rabbits", Am J Obstet Gynecol, Jan. 1965, vol. 91, No. 2, pp. 221-231.

Csapo, A., "The Effects of Ovariectomy and Stretch on the Regulatory Profile and Activity of the Uterus", Prostaglandins, May 1977, vol. 13, No. 5, pp. 965-973.

Garfield, R.E., et al., "Classic Illustration", European Journal of Obstetrics & Gynecology and Reproductive Biology, 1988, vol. 29, pp. 179-180.

Hassan M., et al., "Spatial Analysis of Uterine EMG signals: Evidence of Increased in Synchronization With Term", Conference of the IEEE Eng Med Biol Soc, Sep. 2009, pp. 6296-6299.

Hauth, JC., et al., "Uterine Contraction Pressures With Oxytocin Induction/Augmentation", Obstetrics and Gynecology, Sep. 1986, vol. 68, No. 3, pp. 305-309.

Hurd, WW., et al., "Differential Regulation of Myometrial Prostaglandin Production by Changes in Length", American Journal of Obstetrics & Gynecology, Feb. 2008, 198(2), pp. 225e1-225e4.

Hurd, WW., et al., "Shortening Increases Spontaneous Contractility in Myometrium from Pregnant Women at Term", American Journal of Obstetrics and Gynecology, 2005, 192(4), pp. 1295-1301.

Kawarabayashi T., et al., "Characteristics of Action Potentials and Contractions Evoked by Electrical-field Stimulation of Pregnant Human Myometrium", Gynecol Obstet Investig, 1988, 25(2), pp. 73-79.

Krapohl, AJ., et al., "Uterine Contractions in Spontaneous Labor. A quantitative study", American Journal of Obstetrics and Gynecology, Feb. 1970, vol. 106, No. 3, pp. 378-387.

Lucovnik, M., et al., "Use of Uterine Electromyography to Diagnose Term and Preterm Labor", Acta Obstet Gynecol Scand, Feb. 2011, 90(2), pp. 150-157, First published online Dec. 7, 2010.

Lucovnik, M., et al., "Noninvasive Uterine Electromyography for Prediction of Preterm Labor", American Journal of Obstetrics and Gynecology, Mar. 2011, 204(3), pp. 228e1-228.e10.

Maner, WL., et al., "Predicting Term and Preterm Delivery With Transabdominal Uterine Electromyography", Obstetrics & Gynecology, Jun. 2003, vol. 101, No. 6, pp. 1254-1260.

Miller, SM., et al., "Improved Propagation in Myometrium Associated With Gap Junctions During Parturition", Am J Physiol, 1989, vol. 256, pp. C130-C141.

Osol, G., et al., "Myogenic Tone, Reactivity, and Forced Dilatation: A Three-Phase Model of in vitro Arterial Myogenic Behavior", Am J Physiol, Dec. 2002, vol. 283, pp. H2260-H2267.

Ramon, C., et al., "Synchronization Analysis of the Uterine Magnetic Activity During Contractions", Biomedical Engeering Online 2005, 4:55, 12 pages.

Schlembach, D., et al., "Monitoring the Progress of Pregnancy and Labor Through Electromyography", European Journal of Obstetrics & Gynecology Reproductive Biology, May 2009, 144 Suppl, pp. S33-S39.

Sigger, JN., et al., "Relationship Between Electrical Activity of the Uterus and Surgically Isolated Myometrium in the Pregnant and Nonpregnant Ewe", Journal of Reproduction & Fertility, 1984, 70(1), pp. 103-114.

Takeda, H., "Generation and Propagation of Uterine Activity in Situ", Fertility and Sterility, 1965, vol. 16, No. 1, pp. 113-119.

Veerareddy, S., et al., "Vascular Adaptations to Pregnancy in Mice: Effects on Myogenic Tone", Am J Physiol Heart Circ Physiol, Dec. 2002, vol. 283, pp. H2226-H2233.

Wikland, M., et al., "Relationship Between Electrical and Mechanical Activity of the Isolated Term-Pregnant Human Myometrium", European Journal of Obstetrics & Gynecology Reproductive Biology, 1985, 20(6), pp. 337-346.

Young, RC., et al., "Calcium-Activated Chloride Currents Prolongs the Duration of Contractions in Pregnant Rat Myometrial Tissue", Reproductive Sciences, Aug. 2009, vol. 16, No. 8, pp. 734-739.

Young, RC., et al., "Mechanotransduction in Rat Myometrium: Coordination of Contractions of Electrically and Chemically Isolated Tissues", Reproductive Sciences, 2011, vol. 18, pp. 64-69.

Young, R.C., et al., "Tissue-Level Bioelectrical Signals as the Trigger for Uterine Contractions in Human Pregnancy", J Soc Gynecol Investig, Oct. 2004, vol. 11, No. 7, pp. 478-482.

Young, R.C., "Myocytes, Myometrium, and Uterine Contractions", Annals of the New York Academy of Sciences, 2007, 1101, pp. 72-84.

International Search Report and the Written Opinion, dated Oct. 29, 2012, received in International Patent Application PCT/US2012/029939, 6 pages.

European Search Report and the European Search Opinion received for EP12760496.5, mailed on Sep. 1, 2014, 5 pages.

* cited by examiner 7A                    7B

METHODS OF PREDICTING AND MONITORING LABOR

RELATED APPLICATIONS

This application is a National Stage Filing under U.S.C. 371 of PCT International Application PCT/US2012/029939, filed Mar. 21, 2012 which was published under PCT Article 21(2) in English, which claims benefit under 35 U.S.C. §119 (e) of U.S. Provisional Application No. 61/466,099, filed Mar. 22, 2011, and the entire content of each above-referenced application is incorporated by reference herein in its entirety.

FIELD OF THE INVENTION

The invention relates, in part, to methods for predicting the stage of labor in a pregnant subject.

BACKGROUND

Overall, preterm birth occurs in 1 of every 8 births in the US (March of Dimes; PeriStats), and preterm labor accounts for almost half of those delivered preterm. Prematurity is responsible for $25 billion per year of health expenditures in the US. Health care providers currently must decide whether to transport patients or treat preterm contractions based primarily on the strength and frequency of contractions and the cervical exam. Frequency can be precisely measured using the toco-dynamometer (toco), which measures the shape change of the uterus. Studies have assessed uterine contractions and their relationship to labor; see for example Csapo A., *Obstet Gynecol. Surv.* 1970; 25:515-43, and Ramon C., et al. *Biomed Eng Online* 2005; 4:55. Other investigators have looked at propagation of contractions across the uterus in efforts to identify labor stages; see for example Lucovnik, M., et al. *Acta Obstet. Gynecol. Scand.* 2001 February; 90(2):150-157; Lucovnik, M., et al., *Am J Obstet. Gynecol.* 2011 March; 204(3):228e1-228.10; and Schlembach, D. et al., *Eur J Obstet. Gynecol. Reprod Biol.* 2009 May; 144 Suppl 1:S33-9. Epub 2009 Mar. 17. But non-invasive, accessible, accurate, and inexpensive methods to determine labor status remain elusive.

Clinically, a diagnosis of preterm labor is currently made by considering only the frequency and strength of contractions and the cervical exam, which does not permit an accurate assessment of whether or not a subject is in true labor. Some women seem to experience strong, relatively frequent contractions but the contractions do not change their cervix. Others experience cervical change with only infrequent, moderate contractions. Thus, measuring frequency and strength of contractions does not permit accurate assessment of labor status.

SUMMARY OF THE CLAIMS

It has now been discovered that multichannel assessment of uterine EMG can be used to determine regional cooperation by the human uterus to achieve organ-level coordination of contractions in labor. In addition to the use of recording and ground electrode pairs, it has now been determined that isolated multichannel recording can be performed utilizing an active electrode in one electrode pair as the reference ground for another active electrode, and that this enables accurate and cost-effective determination of labor status in pregnant subjects.

According to one aspect of the invention, methods of determining labor status in a pregnant subject are provided. The methods include (a) measuring uterine muscle contractions in three or more predetermined regions of the subject's uterine wall, (b) detecting a regional synchronization pattern of the uterine muscle contractions in the three or more regions, and (c) assessing the regional synchronization pattern of the uterine muscle contractions as a determination of the subject's labor status. In some embodiments, the synchronization is temporal synchronization. In some embodiments, assessing the regional synchronization pattern includes comparing the regional synchronization pattern of the muscle contractions to a control regional synchronization pattern. In certain embodiments, the method also includes measuring strength and frequency of the uterine muscle contractions in the at least three predetermined regions; and assessing the regional synchronization pattern, strength, and frequency of the uterine contractions as a determination of the status of labor in the subject. In some embodiments, the uterine contractions in the subject are measured in 3, 4, 5, 6, 7, 8, 9, 10, 11, or 12 predetermined regions of the uterine wall. In some embodiments, detecting the regional synchronization pattern includes determining a synchronization factor of the uterine muscle contractions. In certain embodiments, the uterine muscle contractions are measured using electromyography (EMG). In some embodiments, the uterine muscle contractions are measured using recording electrode pairs. In some embodiments, the recording electrode pairs are external recording electrode pairs positioned on the surface of the subject's abdomen. In certain embodiments, a recording electrode pair includes a ground electrode and a recording electrode. In some embodiments, the uterine muscle contraction measurements in each of the three or more regions are obtained using recording electrode pairs that are independent of each other. In some embodiments, the uterine muscle contraction measurements in two or more of the three or more regions of the subject's uterine wall are obtained using recording electrode pairs that share a ground electrode. In some embodiments, the ground electrode is shared by 2, 3, 4, 5, 6, 7, 8, 9, 10, 11, or 12 recording electrodes. In certain embodiments, the electrodes pairs are positioned on the subject's abdomen in a manner minimizing or eliminating overlap of a signal of a uterine muscle contraction measured by two or more of the positioned electrode pairs. In some embodiments, the strength of the contraction is measured at the peak uterine pressure generated by the contraction. In some embodiments, the labor status is absent, latent phase labor, active phase labor, delivery of the baby, or afterbirth-delivery. In certain embodiments, the subject has been, is currently, or will be administered one or more labor-enhancing treatments. In some embodiments, the method also includes subtracting a signal recorded at a first electrode from the signal recorded at least one additional electrode to determine the physical site of origination of the signal in the uterine wall. In some embodiments, the labor-enhancing treatment includes administering a medicament or a physical treatment. In certain embodiments, the physical treatment includes cervical ripening, membrane stripping, or mechanical ripening. In some embodiments, the mechanical ripening is ripening using a balloon catheter or other physical agent used to mechanically dilate the cervix. In some embodiments, the medicament includes a prostaglandin agonist agent or oxytocin. In certain embodiments, the subject has been, is currently, or will be administered one or more labor-inhibiting treatments. In some embodiments, the labor-inhibiting treatment includes administration of medicament, or a physical treatment. In some embodiments, the medicament includes an oxytocin antagonist, magnesium sulfate, a beta-adrenergic agonist, a calcium channel antagonist, or an inhibitor of the prostaglandin system. In some embodiments, the physical treatment includes bed rest or Trendelenberg positioning. In certain embodiments, the measuring of uterine muscle contractions includes remote measuring. In some embodiments, the remote measuring includes data transfer from the subject to a remote site using a telephone, Wi-Fi, or computer. In some embodiments, the determining labor status includes determining whether the subject is in true labor or false labor. In certain embodiments, the method also includes determining the stage of labor in a subject determined to be in true labor. In some embodiments, the stage of labor is first stage labor, second stage labor, or third stage labor. In some embodiments, the first stage labor is latent phase labor or active phase labor. In some embodiments, the second stage labor includes exit of the baby from the subject. In certain embodiments, the third stage labor includes expulsion of the afterbirth from the subject. In some embodiments, the method also includes using the labor status to diagnose or help diagnose a medical condition in the subject. In some embodiments, the medical condition is false labor. In certain embodiments, the medical condition is premature labor. In some embodiments, the medical condition is failure-to-progress in labor.

According to another aspect of the invention, methods of selecting a treatment for a pregnant subject are provided. The methods include using any of the aforementioned methods of the forgoing aspect of the invention to determine the labor status of the subject and selecting a treatment for the subject based at least in part on the determined labor status. In some embodiments, the treatment includes initiating or increasing a labor-enhancing treatment. In certain embodiments, the labor-enhancing treatment includes administering a medicament or a physical treatment. In some embodiments, the physical treatment includes cervical ripening, membrane stripping, or mechanical ripening. In some embodiments, the mechanical ripening is ripening using a balloon catheter or other physical agent used to mechanically dilate the cervix. In certain embodiments, the medicament includes a prostaglandin agonist agent or oxytocin. In some embodiments, the treatment includes initiating or increasing a labor-inhibiting treatment. In some embodiments, the labor-inhibiting treatment includes administration of medicament, or a physical treatment. In some embodiments, the medicament includes an oxytocin antagonist, magnesium sulfate, a beta-adrenergic agonist, a calcium channel antagonist, or an inhibitor of the prostaglandin system. In certain embodiments, the physical treatment includes bed rest or Trendelenberg positioning. In some embodiments, the treatment includes reducing or eliminating a labor-enhancing or labor-inhibiting treatment. In some embodiments, selecting the treatment includes making a decision to increase, decrease, or maintain administration of one or more labor-enhancing medications or treatments during induction of labor for other clinical indications. In certain embodiments, selecting the treatment includes making a decision to increase, decrease, or maintain administration of one or more labor-inhibiting medications or treatments in a subject.

The present invention is not intended to be limited to a system or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

BRIEF DESCRIPTION OF THE DRAWINGS

FIG. 7A shows a single ground electrode used in conjunction with four recording electrodes, one in each of 4 quadrants of the abdomen. FIG. 7B shows 4 separate pairs of electrodes each of which includes one ground and one recording electrode, positioned with one pair in each of 4 quadrants of the abdomen.

FIG. 8A-C shows three examples of unsynchronized signals, and FIG. 8D shows an example of a fully synchronized contraction.

DETAILED DESCRIPTION

Figure 1:
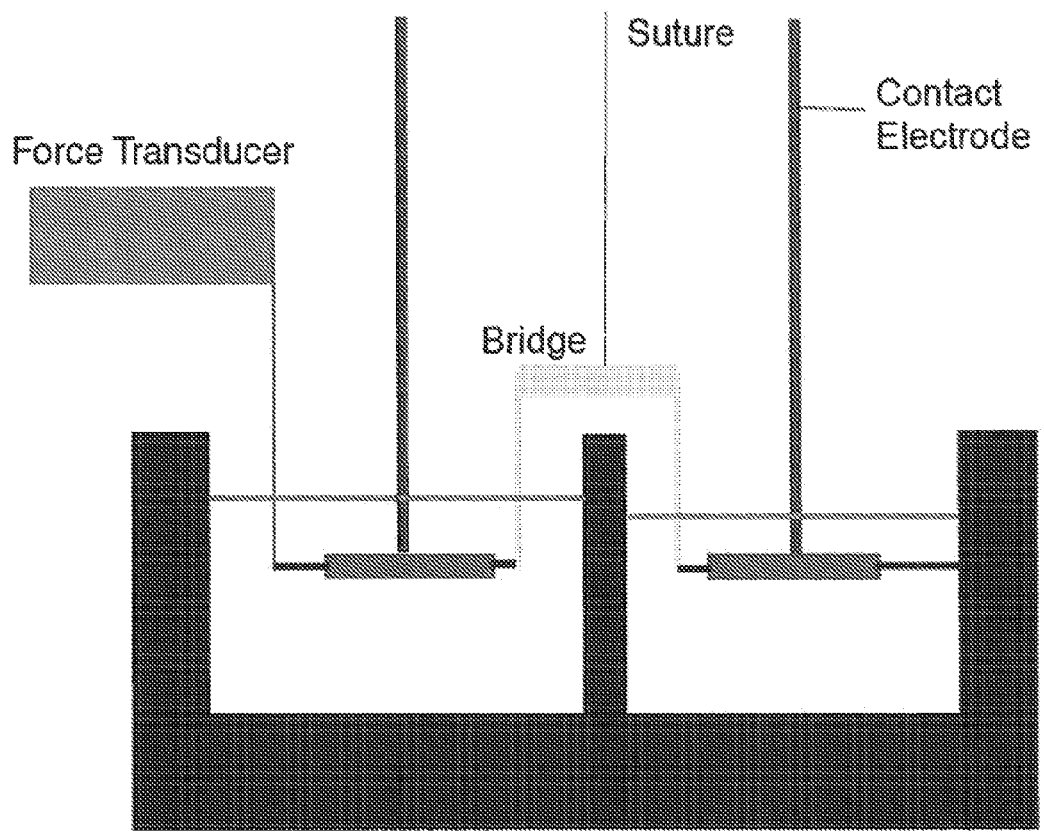
FIG. 1 shows an exemplary dual bath contractility apparatus. A 3-mm barrier separates the two chambers. Transmission of mechanical forces between the tissues was accomplished using a rigid, electrically inert bridge, suspended with a 25-cm suture. A single tension transducer measured the forces generated by the two tissues. One extracellular contact electrode was applied to each tissue, and bioelectrical signals were recorded using independent amplifiers.

Methods set forth herein utilize a novel clinical variable to help differentiate between true labor and false labor. Methods of the invention are based, in part, on an organ-level model of how the uterus generates intrauterine pressure through coordination of regional contractions of the uterus. Prior methods of assessing labor have relied on contraction measurements such as contraction frequency and strength. It has now been identified that a third parameter, organ-level coordination of contractions, e.g. synchronization of contractions, is necessary for true labor and that a combination of measurements of synchronization of contractions with measurements of contraction frequency and/or strength can be used to determine the status of labor or non-labor in a pregnant subject.

Methods presented herein are based, in part, on a novel method of recording using multichannel uterine electromyography (uEMG), and novel methods for evaluation of the data obtained. Previous EMG studies assessing labor have averaged the signals from recording electrodes in order to reduce noise when compared to the single electrode pair. Some investigators have proposed that rates of propagation of EMG signal across the uterus as key to understanding labor (see for example, Lucovnik, M., et al. *Acta Obstet. Gynecol. Scand.* 2001 February; 90(2):150-157; Lucovnik, M., et al., *Am J Obstet. Gynecol.* 2011 March; 204(3):228e1-228.10; and Schlembach, D. et al., *Eur J Obstet. Gynecol. Reprod Biol.* 2009 May; 144 Suppl 1:S33-9. Epub 2009 Mar. 17. In contrast to previous work, some of which utilized two pairs of electrodes and measured the delay between the signals recorded at each recording electrode site to obtain a propagation velocity, methods of the present invention do not assume that the same signal is transmitted from one location to the other, but rather that signals uniquely arise from each site, and then remain local without propagation. It has now been discovered that surprisingly, by measuring the overlap of the signals (i.e. synchronization) obtained from multiple recording electrode sites rather than the delay between signals recorded at two sites, the status of labor in a pregnant subject can be accurately determined.

Methods of the invention are based, in part, on the concept that the uterus functions as the summation of regions that can be macroscopically examined, and that it is the synchronization of the regional contractions that dilates the human cervix and causes labor. These concepts have now been examined at the cellular and tissue-level function of uterine contractility. These concepts significantly depart from the previously accepted mechanism that the uterus contracts in a manner similar to peristalsis, where electrical signals track linearly through the uterus. Methods of the invention are based, in part, on recognition of the importance of synchronization of regional uterine muscle contractions and the unexpected recognition that synchronization of contractions in conjunction with strength and frequency of the contractions can provide a means to assess the effectiveness and status of mammalian labor.

Labor is the process of birth and is considered to include three stages. In the first stage, uterine contractions cause the cervix to thin and dilate (open) from 0 to about 10 cm. Contractions that are not forceful or coordinated enough to open the cervix may indicate the woman is not in labor but is instead in "false labor". The first stage of true labor can be subdivided into the "early" phase (also known as "latent" phase) and the "active" phase. Uterine muscle contractions increase in strength and duration as labor progresses from the early phase into the active phase. Contractions in the active phase are generally more frequent and stronger than contractions in the early or latent phase and during the active phase the cervix dilates to 8-10 cm. The second stage of labor includes stronger uterine contractions that serve to push the baby out through the birth canal. After the birth, the third and final stage of labor occurs. The third stage of labor includes uterine muscle contractions that effectively expel the afterbirth (e.g., the placenta and remaining fetal membranes) from the uterus. Labor contractions include uterine muscle contractions that are effective to dilate the cervix in true labor. In contrast, non-labor contractions or false-labor contractions are uterine muscle contractions that do not dilate the cervix.

Methods of the invention can be used to identify very early labor both at term and in pre-term pregnancies. It has previously not been possible to accurately identify whether subjects exhibiting symptoms of early labor were truly in labor or were in false labor. Methods of the invention permit early identification of labor as real or false and can indicate a need for a therapy to be started prior to any cervical change, thus permitting early intervention in the pregnancy if necessary. Methods of the invention are also useful for monitoring labor status which can aid a health care provider in the selection or modification of a treatment for a pregnant subject, for example a treatment to enhance or inhibit labor.

Methods set forth herein provide non-invasive techniques useful to accurately measure and assess organ-level coordination of uterine contractions. Methods of the invention permit such measurements to be used in conjunction with information on contraction frequency and strength to determine labor status in a subject. The combination of frequency, strength, and uterine coordination (synchronization) provides a more complete assessment of uterine contractility and labor status, than has been previously available. Although not intending to be bound by a particular theory, it is believed that in addition to the strength and frequency of uterine muscle contractions, the synchronization of contractions of uterine muscles is necessary to increase intrauterine pressure, thin and dilate the cervix, as well to expel the baby and the afterbirth from the uterus.

Additional clinical applications of methods of the invention used in preterm labor include: assessing uterine contractions on an ongoing basis to assist with management of patients at high risk for preterm labor; and assessing the efficacy of tocolytic therapy in patients with documented preterm labor.

In addition to use in preterm labor, methods of the invention may also be used in pregnancy conditions including, but not limited to: the clinical assessment of arrest of active labor (associated with increases of Cesarean Section rates); minute-by-minute assessment of the clinical efficacy of oxytocin administration (associated with fetal distress, uterine rupture and increased Cesarean Section rates); and to provide information on coordination of uterine contractions that may directly lead to improved knowledge of the physiology of labor at the organ-level, and ultimately lead to development of methods to control uterine contractility.

In some embodiments, methods of assessing labor status set forth herein utilize multichannel uterine electromyography (uEMG) to determine the presence or absence and/or relative timing of regional uterine muscle contractions. Prior uses of multichannel uEMG recordings have failed to identify or relate relationships among electrode synchronization, the generation of intrauterine pressures, and progression to true labor. Prior uEMG methods also required significantly complex equipment such as the SARA device to assess synchronization of the contractions. (see Ramon, C. et al., *Biomed Eng Online* 2005; 4:55). The SARA device includes an array of superconducting quantum interference devices (SQUID). The SQUID Array for Reproductive Assessment (SARA) is made from 151 probes spaced 2.5 cm apart. The SARA is expensive to purchase and run, immobilizes the patient during the assessment, requires extensive post-hoc data analysis, and is therefore not practical for routine use.

Alternative existing labor status tests are also limited. For example, fetal fibronectin tests of labor status are clinically useful if the results are negative (this indicates the patient is not in true labor). But positive results do not necessarily indicate the patient is in labor. Additionally, results are obscured by bleeding, a recent cervical exam, and recent coitus. Methods of the invention disclosed herein overcome prior limitations and permit assessment of labor with a good specificity for true labor (i.e., are diagnostic of false labor), good sensitivity and can be used regardless of bleeding or cervical manipulation history, can be performed in a convenient setting (e.g., home, clinic, hospital, office, or any other patient location) and at relatively low cost.

Methods of the invention use uEMG measurements to assess uterine coordination and interpret the results through a novel model of uterine function. The uterus generates 50 to 75 torr peak pressures with each contraction, and the clinical measurement of adequate labor is through summation of these pressures over 10-minute time intervals (Krapohl, A. J. et al. Am J. Obstet Gynecol 1970; 106; 378-87 (Montevideo units). Methods set forth herein are based on the recognition that along with the frequency and strength of contractions, a third parameter of uterine contractility is necessary for true labor to occur—organ-level coordination of contractions.

A key factor in accurately assessing labor status and the likelihood of delivery is organ-level coordination of uterine contractions. It has been determined that "synchronization" of contractions results when most uterine muscle regions are simultaneously active at the peak of the contraction. For example, in some embodiments of the invention the synchronization of contractions can be defined as present when at least 50% 60%, 70%, 80%, 85%, 90%, 95%, 96%, 97%, 98%, 99%, or 100% of recorded uterine muscle regions in a subject are simultaneously active at the peak of the contraction. Thus, for example, in an embodiment of the invention in which a pregnant subject's abdomen is divided into 12 regions from which uterine muscle contractions are recorded, and synchronization of contractions is determined to be present in 6, 7, 8, 9, 10, 11, or 12 of the regions, indicating that at least 50% of the regions have synchronized contractions. The determined synchronization of contractions in the regions, when present in conjunction with sufficient levels of contraction strength and frequency indicate the subject is in true labor. In the same subject, with the same electrode array, a determination that 6, 7, 8, 9, 10, 11, or 12 of the regions lack synchronization of contractions may indicate that the subject is not in true labor, even if measured contraction strength and frequency levels are sufficiently high to suggest true labor.

It will be understood that in embodiments of the invention in which recordings are obtained from fewer regions of a pregnant subject's abdomen (e.g., 11, 10, 9, 8, 7, 6, or 5 regions) the synchronization of contractions in a lower number of regions may indicate true labor, as compared to when recordings are made from a higher number of regions. For example, if an embodiment of the invention a pregnant subject's abdomen is divided into 6 regions from which muscle contractions are recorded, and synchronization of contractions is determined to be present in at least 4, 5, or 6 regions, the subject may be in true labor. Similarly, a lack of synchronization of contractions determined in 3, 4, 5, or 6 regions may indicate that the subject is not in true labor.

Methods of the invention permit determination of the degree of organ-level coordination of each contraction, which is referred to here as the synchronization factor (SF).

Methods of the invention may include detecting a regional synchronization pattern by determining a synchronization factor (SF) of the uterine muscle contractions. As used herein, the term "pattern" and "SF" used in reference to synchronization of muscle contractions means temporal arrangement of contractions. In some methods of the invention, a synchronization factor (SF) is the sum of signal duration of all electrodes/number of electrodes×signal duration of the contraction. The value of SF using this calculation varies between ~0 (unsynchronized) and 1.0 (fully synchronized) for each contraction. Using probability equations, the SF value can be combined with the frequency of contractions and the relative strength of contractions to create a composite "Labor Status" variable. It will be understood that the combination off, s, and SF can be used to assess labor status using methods provided herein, and that tabular ranges for f, s, and SF provided herein are exemplary values.

In some embodiments of the invention, Labor Status (LS) may be calculated using Equation 1 in which "f" multiplied by "s" multiplied by "SF" equals "LS". In such embodiments a table can be used to assess the Labor Status:

TABLE 1

Exemplary values for f, s, and SF for labor status determination. (Cx = contractions)

| f (Cx/hour) | s (strength) | SF (synchronization factor) |
|---|---|---|
| 0 → 0 | weak → 0 | (range is 0 to 1, |
| 1 → .1 | mild → .2 | the measured value) |
| 2 → .2 | moderate → .6 | |
| 3 → .3 | strong → 1 | |
| 4 → .4 | | |
| 5 → .5 | | |
| 6 → .6 | | |
| 7 → .7 | | |
| 8 → .8 | | |
| 9 → .9 | | |
| 10 → 1 | | |

In some embodiments of the invention, a combination of frequency, strength, and SF is used to assess the labor status of a subject. As a non-limiting example, in Subject A, 15 minutes has elapsed since the prior contraction (4 Cx/hr; f=0.4), strength is moderate (s=0.6), and SF is measured to be 0.5. Based on the data obtained from the subject, Labor Status is determined to be 0.4 times 0.6 times 0.5=0.12, suggesting the subject is not in labor. As another non-limiting example, 6 minutes elapse since prior contraction (10 Cx/hr; f=1), strong contractions (s=1), SF is 0.9. Based on the data obtained from the subject, Labor Status is determined to be 1 times 1 times 0.9=0.9, suggesting the subject is in labor.

In some embodiments of the invention, additional detail may be added to a Labor Status determination using a more detailed equation. As a non-limiting example, if the contraction frequency is greater than four contractions per hour there is no dependence on further increases in contraction frequency and an equation such as IF (f>0.4) THEN (Labor Status="s" multiplied by "SF"), may be used. In some embodiments of the invention, strength of contractions may be indicated using a scale from 0 to 1.0 such as the scale shown in Table 2. It will be understood that the scale shown in Table 2 is exemplary, and that relative scales for contraction strength may be used in methods of the invention.

TABLE 2

Exemplary scale of contraction strength

| | |
|---|---|
| No contractions (absent) = | 0 |
| Weak contractions = | .1 to .3 |
| Moderate contractions = | .4 to .7 |
| Strong contractions = | .8 or .9 |
| Maximum strength contraction = | 1.0. |

Methods of the invention may combine SF with contraction frequency and strength parameters, resulting in a composite parameter, referred to herein as a "Labor Status" of the pregnant subject, which is more predictive of delivery than frequency and strength alone.

The invention, in part, includes methods to determine the labor status in a pregnant subject. As used herein the term "subject" also referred to herein as a "patient" means a mammal, including, but not limited to primates, non-human primates, dogs, horses, cats, ungulates, etc. A primate subject of the invention may be a human subject. Exemplary non-human mammals include, but are not limited to farm animals, zoo animals, etc. and methods of the invention are envisioned for human and veterinary practice.

As used herein the term "Labor Status" may include the status of a pregnant subject prior to the onset of true labor (e.g. pre-labor, non-labor). A subject in pre-labor may be a subject undergoing uterine muscle contractions that are not true labor contractions, but are for example, false labor contractions, Braxton-Hicks contractions and the like. Thus, one exemplary labor status of a subject that can be determined using methods of the invention may be "non-labor" where the subject is not in labor. Other examples of a labor status that can be determined using methods of the invention include, but are not limited to latent phase labor, active phase labor, and afterbirth labor, etc. Those skilled in the art will recognize that there are additional terms for stages of labor, and that methods described herein can be used to determine at least (1) whether or not a subject is in labor and/or (2) the stage of the subject's labor (e.g., latent phase, active phase, etc.). An additional stage of labor that can be assessed using methods of the invention is post-delivery labor, for example, after the baby is delivered, the labor remaining for expulsion of the placenta or afterbirth.

Methods of the invention are useful to assess pre-term (gestational ages 24 to 37 weeks), term (38 to 41 weeks), and post-term (>41 weeks) labor status in a pregnant human subject. It will be understood that different mammals have different gestational periods and so the timing of pre-term, term, and post-term will vary depending on the species. Methods provided herewith can be used to monitor and assess the status of a normal labor event, beginning before or during the labor; select or help selected a medical treatment for a pregnant subject, and can also be used to monitor and assess the status of labor associated with a medical intervention such as induction or actions to inhibit labor in a subject.

Methods of the invention can be used to assess labor status in a pregnant subject who has been, is currently, or will be administered one or more labor-enhancing treatments. As used herein, the term "labor-enhancing treatment" means an action, drug regimen, or procedure intended to enhance the onset or maintenance of labor in a subject. Thus, methods of the invention can be used to monitor labor status in a subject before, during, and/or after the subject is administered a medicament or a physical treatment to enhance the subject's labor. As used herein, the term "enhance labor" includes methods to initiate, speed up, and/or maintain labor. Such methods include, but are not limited to: cervical ripening, membrane stripping, mechanical ripening as with a balloon catheter, chemical ripening as with prostaglandin agonist agent or oxytocin administration, etc. Additional labor enhancing methods, including procedures and medicaments will be known to those skilled in the art.

Methods of the invention can also be used to assess labor status in a pregnant subject who has been, is currently, or will be administered one or more labor-inhibiting treatments. As used herein, the term "labor-inhibiting treatment" means an action, drug regimen, or procedure intended to inhibit the onset or maintenance of labor in a subject. Thus, methods of the invention can be used to monitor labor status in a subject before, during, and/or after the subject is administered a medicament or a physical treatment to inhibit the subject's labor. As used herein, the term "inhibit labor" includes methods to delay the onset of, and/or stop the progress of, and/or slow the progress of labor in a subject. Such methods include, but are not limited to: administration of an oxytocin antagonist, magnesium sulfate, beta-adrenergic agonist, calcium channel antagonist, or inhibitor of the prostaglandin system, etc., or a physical treatment, such as but not limited to bed rest or Trendelenberg positioning, etc. Additional labor inhibiting methods, including procedures and medicaments will be known to those skilled in the art.

Methods of the invention also can be used to diagnose or help diagnose a medical condition in the subject. For example, by determining the labor status in a subject, a healthcare professional can determine whether the subject is in true labor and should seek aid from a healthcare professional or other individual. Similarly, methods of the invention can permit determination of medical conditions such as false labor, premature labor, failure-to-progress in labor, slowed labor, etc. By using methods of the invention to determine labor status and/or to identify a medical condition in a pregnant subject, an appropriate treatment strategy for the subject may be selected. Treatments for pregnant subjects having medical conditions such as preterm labor, false labor, failure to progress etc., are well known to those skilled in the art.

Some medical treatments that may be selected based at least in part on a subject's labor status information obtained using a method of the invention may include administration of one or more labor-enhancing medicaments and/or physical treatments. Labor-enhancing treatments may be initiated, increased, decreased, or halted based on labor status information obtained using methods of the invention. Examples of physical treatments include but are not limited to cervical ripening, membrane stripping, or mechanical ripening. A non-limiting example of a medicament treatment to enhance labor includes administration of a prostaglandin agonist agent or oxytocin.

Additional examples of medical treatments that may be selected based at least in part on a subject's labor status information obtained using a method of the invention may include administration of one or more labor-inhibiting medicaments and/or physical treatments. Labor-inhibiting treatments may be initiated, increased, decreased, or halted based on labor status information obtained using methods of the invention. Examples of labor-inhibiting medicaments include but are not limited to an oxytocin antagonist, magnesium sulfate, a beta-adrenergic agonist, a calcium channel antagonist, or an inhibitor of the prostaglandin system. Examples of labor-inhibiting physical treatments may include but are not limited to bed rest or Trendelenberg positioning. In some aspects of the invention, methods of determining a labor status permit selection of a treatment that includes reducing or eliminating a labor-enhancing or labor-inhibiting treatment.

Methods of the invention may also be used in some embodiments of the invention to assist a health care professional in making a decision to increase, decrease, or maintain administration of one or more labor-enhancing medications or treatments during induction of labor. In some embodiments, the labor induction is preformed based on a clinical indication. In some embodiments, methods of the invention for determining labor status in a subject may be used to select or to aid in the selection of a treatment used to slow or halt labor in a subject. In such embodiments, selecting or aiding in the selection may include a decision to increase, decrease, or maintain administration of one or more labor-inhibiting medications or treatments in a subject.

Methods of the invention, in some embodiments, include measuring uterine muscle contractions in at least 3, 4, 5, 6, 7, 8, 9, 10, 11, 12, 13, 14, or 15 predetermined regions of the subject's uterine wall; detecting a regional synchronization pattern of the underlying uterine muscle contractions in the at least 3, 4, 5, 6, 7, 8, 9, 10, 11, 12, 13, 14, or 15 regions, respectively; and assessing the regional synchronization pattern of the underlying uterine muscle contractions as a determination of the subject's labor status. Some embodiments of the invention include measuring uterine muscle contractions in five or more regions of the subject's uterine wall, detecting a synchronization pattern in the regions in the five or more regions; and assessing the regional synchronization pattern in view of the strength and frequency of the contractions as a determination of the subject's labor status.

Methods of the invention may include measuring regional contraction activity of the uterus using surface electrodes positioned on the subject's abdomen. Thus, for example, measuring contractions of three regions of the uterine wall may comprise measuring contractions using surface electrodes positioned on three corresponding regions of the subject's abdomen. Additional numbers of electrodes and their positioning on subjects' abdomens are encompassed by methods of the invention. For example, an electrode pair positioned on the right upper front quadrant of a subject's abdomen can be used to measure contractions in the right upper front quadrant of the subject's uterus. An electrode pair positioned on the left upper front quadrant of a subject's abdomen can be used to measure contractions in the left upper front quadrant of the subject's uterus. An electrode pair positioned on the right lower front quadrant of a subject's abdomen can be used to measure contractions in the right lower front quadrant of the subject's uterus and an electrode pair positioned on the left lower front quadrant of a subject's abdomen can be used to measure contractions in the left lower front quadrant of the subject's uterus. Each electrode pair can be separated from the other electrodes to minimize signal cross-talk so that each region of the uterus can be measured independently.

In some embodiments of the invention, the surface of the subject's abdomen is divided into at least 3, 4, 5, 6, 7, 8, 9, 10, 11, 12, 13, 14, or 15 distinct, non-overlapping areas, from which contractions of the underlying uterine wall regions can be measured using EMG electrodes. Two or more of the areas may be similar to each other in size and/or shape. Two or more of the areas may be different from each other in size and/or shape. In certain embodiments EMG electrodes are placed in a manner permitting measurement in five or more distinct, non-overlapping regions. The number of recording regions may be selected based on various factors. Non-limiting examples of factors that may be considered when selecting the number of recording regions and placement of electrodes may include space constraints in the size of the subject's abdomen, (e.g., limited by desired distance between the recording electrodes, etc), minimizing the number of recording electrodes positioned on a subject, limiting expense and time for electrode placement, obtaining recordings from non-overlapping regions, etc.

In certain embodiments of the invention, the surface of the subject's abdomen is divided into at least 3, 4, 5, 6, 7, 8, 9, 10, 11, 12, 13, 14, or 15 regions from which contractions of the underlying uterine wall regions may be measured using EMG electrodes, and two, three, four, five, six, seven, eight, nine, ten, eleven, twelve or more of the abdominal regions may overlap with one or more other abdominal regions. Two or more of the regions may be similar to each other in size and/or shape, but need not be. In certain embodiments of the invention, two or more recording regions may overlap and a value determined from one recording electrode may be subtracted from a value determined from a second recording electrode as described elsewhere herein, to determine a measure of synchronization of contractions in the uterine regions represented by the recording regions.

It will be understood that regional overlap may be a physical artifact of placing a finite number of electrodes across the surface of the abdomen. In some embodiments of the invention, signals from different electrodes may be of exactly the same frequency, but appearing less in magnitude in one of the two electrodes. This may under certain conditions be seen to be the same signal recorded from two locations. In such situations, the larger signal may be scaled down in magnitude and subtracted from the smaller signal, rendering the smaller signal more representative of the intended region.

Methods of the invention may include measuring regional muscle contractions in a subject as a determination of a pattern of regional synchronization of muscle contractions and a synchronization factor (SF) in the subject. The synchronization of uterine muscle contractions may be a temporal synchronization, which includes synchronized timing of the onset and release of contractions in the uterine muscle regions. A synchronization pattern and SF determined in the subject can be compared to a control synchronization pattern or SF of regional synchronization pattern of muscle contractions. Thus, for a subject, a synchronization pattern or SF that is statistically the same as a control synchronization pattern or SF for non-labor is an indicator of non-labor as the labor status of the subject. Similarly, for a subject, a synchronization pattern or SF that is statistically the same as a control synchronization pattern of SF for true labor (e.g., latent labor, active labor, etc.) is an indicator of true labor status (e.g., latent labor or active labor etc.) of the subject.

Non-limiting exemplary ways to determine labor status using measures of frequency, strength, and synchronization of uterine muscle contractions with methods of the invention are provided in the Examples section. In some embodiments of the invention, contractions are characterized by three parameters, f (frequency of contractions per hour), s (strength), and a Synchronization Factor (SF). In some aspects of the invention, these three parameters are not independently sufficient to determine labor status and each may be equally weighted when determining labor status using methods of the invention.

Synchronization patterns of uterine contractions in regions of the uterus; a synchronization factor (SF) determined for a synchronization pattern; and/or a combination of SF with contraction strength and frequency each may be compared to control values for synchronization patterns, synchronization factor (SF), and combinations of SF with contraction strength and frequency, respectively. A control may be a predetermined value, which can take a variety of forms. It can be a single cut-off value, such as a median or mean. It can be established based upon comparative groups, such as in groups at a particular stage of labor and groups in false labor. Another example of comparative groups would be groups having a particular treatment to enhance or inhibit labor. Thus, a synchronization pattern in a pregnant subject can be compared to one or more control values for synchronization patterns from a stage of labor or from pre-labor (non-labor). Similarly, an SF value determined for a pregnant subject can be compared to one or more SF control values from a stage of labor or from pre-labor (non-labor), and a combination of SF, contraction strength, and contraction frequency, can be compared to one or more control values for SF, contraction strength, and contraction frequency.

A predetermined synchronization pattern, SF, or a combination of SF with contraction frequency and strength, will depend upon the particular status of the labor in the population selected. For example, control synchronization pattern determined based on a population in non-labor will be a different contraction synchronization pattern than that of a control determined based on a population in latent stage labor. Both will also differ from a control contraction synchronization pattern determined based on a population in active labor. Accordingly, the predetermined synchronization pattern selected may take into account the category in which an individual falls. Appropriate ranges and categories can be selected with no more than routine experimentation by those of ordinary skill in the art. Comparing a uterine contraction synchronization pattern of a subject determined using methods of the invention, with that of a control value, can assist and/or allow a health care provider to determine the status of labor in the subject.

Similarly, a control SF determined based on a population in non-labor will be a different SF than that of a control determined based on a population in latent stage labor. Both will also differ from a control SF determined based on a population in active labor. Accordingly, the predetermined SF selected may take into account the category in which an individual falls. Appropriate ranges and categories can be selected with no more than routine experimentation by those of ordinary skill in the art. Comparing an SF of a subject determined using methods of the invention, with that of a control value, can assist and/or enable a health care provider to determine the status of labor in the subject.

Similarly, a control combination of SF with contraction frequency and strength determined based on a population in non-labor will be a different combination of SF with contraction frequency and strength than that of a control determined based on a population in latent stage labor. Both will also differ from a control combination of SF with contraction frequency and strength determined based on a population in active labor. Accordingly, the predetermined combination of SF with contraction frequency and strength may take into account the category in which an individual falls. Appropriate ranges and categories can be selected with no more than routine experimentation by those of ordinary skill in the art. Comparing a combination of SF with contraction frequency and strength for a subject determined using methods of the invention, with that of a control value, can assist and/or enable a health care provider to determine the status of labor in the subject.

Typically a control will be based on labor status of apparently normal individuals before and during labor, but a control may also be based on labor status of individuals whose labor has been enhanced, inhibited, or is pre-term or is in another category of abnormal labor. In some aspects of the invention, a subject can serve as her own control. For example, the status of labor can be determined in a pregnant woman and can be compared to the status of labor in the same woman at a subsequent time.

In some embodiments of the invention, 1, 2, 3, 4, 5, 6, 7, 8, 9, or more labor status determinations can be made in a single subject. In certain embodiments of the invention, continuous determinations can be obtained for a single subject across a period of time. Thus, methods of the invention can be used to compare two or more labor status determinations in a single subject as a measure of the onset or progression of labor, or the slowing or stopping of labor in the subject. A non-limiting example of a use of multiple labor status determinations or determinations over time may include an initial determination of labor status of a subject, followed by administration of a medication to induce or to inhibit labor in the subject and a second determination of labor status, which can be compared to the initial labor status for the same subject. Such comparisons permit changes in labor status to be determined and evaluated. It is envisioned that such data can be used by a health care professional to assess labor status in the subject and to help make decisions regarding initiating, increasing, decreasing, stopping, or in other ways modifying medical procedures relating to the subject's pregnancy and labor status.

The percentage or number of regions of synchronization of contractions that indicate true labor versus false labor can be compared to control values for the given number of regions from which recordings are made. For example, a control for a six recording electrode array can be determined by assessing the number of synchronized contractions obtained using the six recording electrode array in a set of pregnant women to determine the number of regions of synchronized contractions in true labor versus the number of regions of synchronized contractions in false labor. Thus, a control value for an a recording electrode array that includes at least 3, 4, 5, 6, 7, 8, 9, 10, 11, or 12 electrodes can be determined and then used to provide a cut-off value or other indication to identify true labor versus false labor in subjects whose contraction synchronization is being measured using at least 3, 4, 5, 6, 7, 8, 9, 10, 11, or 12 recording electrodes, respectively.

Methods of the invention may also include measuring strength and frequency of the uterine muscle contractions in the at least three predetermined regions of the uterus; and assessing the regional synchronization pattern, strength, and frequency of the uterine contractions as a determination of the status of labor in the subject. In some methods of the invention, the strength of a contraction may be measured and interpreted to be that measurement occurring at the peak uterine pressure generated by the contraction. In some embodiments, measurements of strength and frequency of muscle contractions are made in more than three regions. In some aspects of the invention, uterine contractions in the subject are measured in at least 3, 4, 5, 6, 7, 8, 9, 10, 11, or 12 predetermined regions of the uterine wall.

Methods of the invention include measuring uterine muscle contractions using any suitable means including, but not limited to uterine electromyography (uEMG) and ultrasound. uEMG methods used in the invention may comprise detecting and/or recording uterine muscle contractions by means of electrodes. In some aspects of the invention, uterine muscle contractions are measured using recording electrode pairs that can be internal or external electrode pairs. In some methods of the invention, recording electrode pairs are external recording electrode pairs that are positioned on the surface of the subject's abdomen.

An electrode pair used in some methods of the invention is a recording electrode pair that comprises a ground electrode and a recording electrode. Electrode pairs used to measure contractions in a region of a subject's uterus may be positioned on the subject's abdomen in a manner that permits measurement of uterine muscle contraction in the region independent of and with minimal or no cross-contamination or interference from other regions. Methods of the invention may include positioning electrode pairs on a subject's abdomen in a manner to minimize or eliminate overlap of a signal of a uterine muscle contraction measured by two or more of the positioned electrode pairs. In some methods of the invention, each electrode pair includes a ground electrode and a recording electrode that is independent of any other electrode from another pair. Thus, in some embodiments of the invention, uterine muscle contraction measurements in each of the at least 3, 4, 5, 6, 7, 8, 9, 10, 11, or 12 regions are obtained using recording electrode pairs that are independent of each other. In certain embodiments of the invention, uterine muscle contraction measurements in 2 or more of the at least 3, 4, 5, 6, 7, 8, 9, 10, 11, or 12 regions of the subject's uterine wall are obtained using recording electrode pairs that share a ground electrode.

In some embodiments of the invention, a ground electrode is shared between at least 2, 3, 4, 5, 6, 7, 8, 9, 10, 11, 12, 13, 14, or 15 recording electrodes. In certain embodiments, a recording electrode may have a ground electrode that is not shared with any other recording electrode and is not the same ground electrode as that of another recording electrode. Different combinations of recording electrodes with ground electrodes are envisioned for use in embodiments of the invention. In some embodiments, 2, 3, 4, 5, 6, 7, 8, 9, 10, 11, or 12 recording electrodes may be paired with a single ground electrode. As used herein the term "pair" when referring to electrodes means a recording electrode and a ground electrode, the latter of which may be part of a "pair" with more than one recording electrode. For example, ground electrode "A" may be one half of a pair in which the other half is recording electrode "X" and ground electrode "A" may also be one half of a pair in which the other half is recording electrode "Y". In a non-limiting example, there may be 5, 6, 7, 8 or more recording electrodes that share a single ground electrode, which is considered to be a member of 5, 6, 7, 8, or more different electrode pairs, respectively.

A ground electrode (also referred to herein as a reference electrode) in an embodiment of the invention may be positioned on the subject's abdomen or on a non-abdominal area of the subject's body. For example, in some embodiments of the invention, a ground electrode may be positioned on a subject's leg, arm, neck, head, or other non-abdominal location, including a position that is an internal location in the subject. In some embodiments of the invention, a ground electrode may be positioned on a subject's thigh and serve as a ground for recording electrodes positioned on the subject's abdomen.

It has now been identified that the number of channels that can be recorded from a pregnant human uterus may be determined based on the electrode contact pad size and the distance between the pads (4-5 cm). As used herein an "electrode contact pad" is the portion of a recording or ground electrode that is positioned on or in the subject's body. It will be understood that an electrode contact pad for use in methods of the invention may be of any geometric shape including square, circular, oval, rectangle, triangle, etc., or may be an irregular shape. The size of an electrode contact pad useful in methods of the invention may include at least one dimensions of between about 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, 4.0 cm. In some embodiments, a pad may have a size that is about 2.5×2.5 cm. All electrode contact pads used in methods of the invention need not be of the same shape or size. The distance between recording electrode contact pads positioned on a subject can vary but may be at least 3, 4, 5, 6, 7, 8, 9, 10, or more cm from another recording electrode contact pad. In some embodiments, a distance between two or more recording electrode contact pads is 4-5 cm and the pads are about 2.5×2.5 cm in size.

Electrodes used in methods of the invention may be positioned onto a subject in locations selected by a healthcare professional or other party in a manner permitting recording from three or more predetermined regions of the subject's uterine wall. Predetermined regions of the abdominal well may be selected based on variables including but not limited to, the number of recording electrodes to be positioned, number of channels available in an EMG recorder, subject size and/or abdominal shape, positioning of electrodes used to generate control values, convenience, positioning recommendations or mapping data, prior experience of a health care professional, prior experience with the subject, etc.

It is understood that electrode contacts need not be placed in independent pairs on a subject because, as described elsewhere herein, not every recording electrode requires a separate grounding reference that is not paired with a one or more additional recording electrodes. In some embodiments of the invention, data can be obtained and recorded from 3, 4, 5, 6, 7, 8, 9, 10, 11, 12, or more electrodes using a single common ground electrode positioned on the subject. In some embodiments, two or more recording electrodes are utilized with a shared ground electrode and the signals among the electrodes are measured and then subtracted to determine the difference of electrical signals between the different electrode locations. In a non-limiting example, two recording electrodes may share a ground electrode and the signals from the two electrodes are subtracted to determine the difference of electrical signals between the two different electrode locations.

Figure 12:
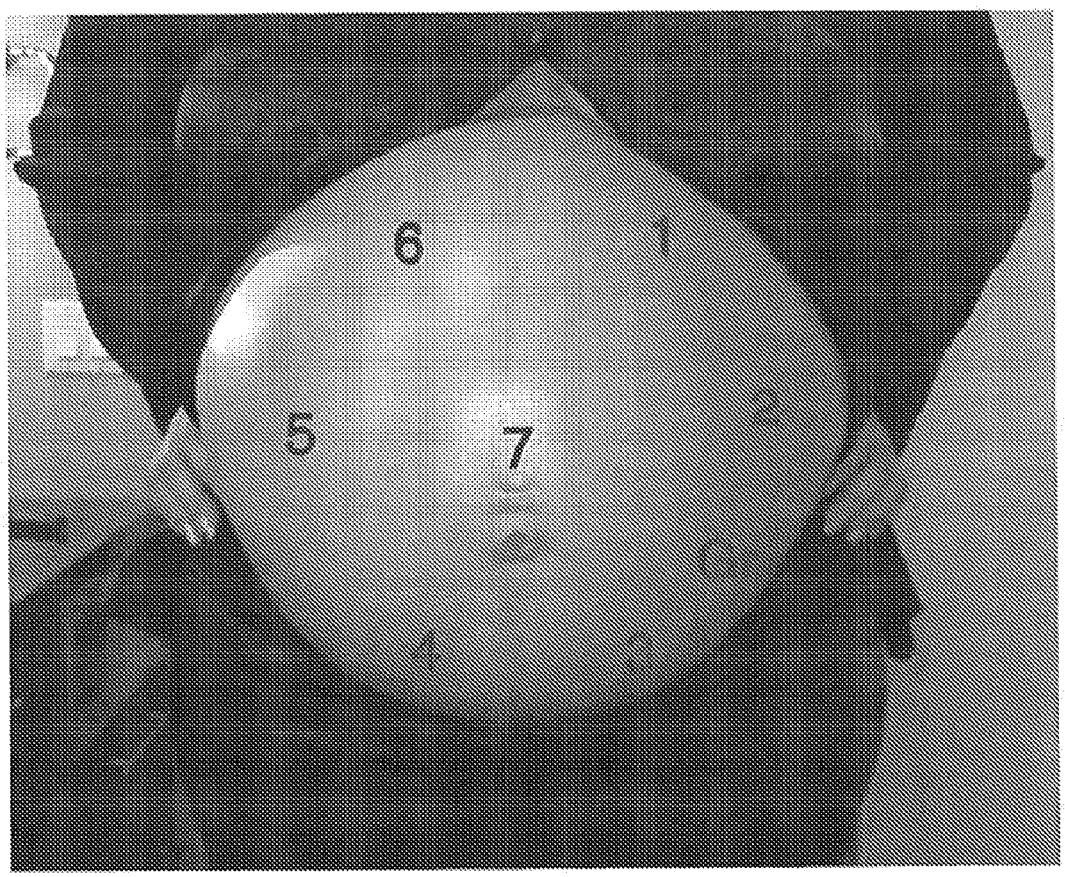
FIG. 12 is a photograph of a pregnant subject showing an example of positions for placement of 7 recording electrodes plus one ground electrode on the subject's abdomen. Gr=ground electrode, numbers 1-7=placement positions for recording electrodes 1-7, respectively.

Shared ground electrode procedures of the invention can utilize the active recording electrode pad of one channel as the ground for another channel, and recordings can be performed in which each recording electrode pad is independently isolated. Channel isolation can be performed using art-known methods, such as using a multi-output operational amplifier for each channel. For example, using a single ground with five recording electrodes permits at least five channel resolution using six pads (one for ground reference). This permits an increase a higher number of effective channels for a given number of recording electrode pads. FIG. 12 shows a non-limiting example of an array of seven recording contact pads and one ground that provides data collection and assessment of twelve regions of uterine wall by placing the array of electrodes over the surface of the pregnant abdomen. For this exemplary arrangement of seven electrodes (plus one ground placed on the patient thigh for example), the following regions can be assessed: 1-2; 2-3; 3-4; 4-5; 5-6; 6-1; 7-1; 7-2; 7-3; 7-4; 7-5; and 7-6. (total of twelve regions with only eight contact pads). Note that in this example, electrode 7 will require six independent reference outputs, and each of the other channels will require three independent reference outputs. Using routine methods in conjunction with the teaching provided herein, a skilled artisan can position recording electrodes and ground electrodes on a subject and be able to assess signals in a manner suitable for use in embodiments of the invention.

Methods of the invention may include obtaining measurements of uterine contractions from a subject, wherein the subject is in a health care facility, such as a clinic, hospital, physician's office, etc. Methods of the invention also encompass use of remote measurement means and apparatus to obtain measurements and data from subjects and deliver the measurements and/or data to a location or device that is remote from (e.g., not physically located at or near the subject). Thus, methods of the invention can be used to determine labor status of a subject located within a health care facility, or outside a health care facility, for example a subject at home, traveling, etc. In some embodiments of the invention, recording electrodes and one or more ground electrodes may be placed on a subject and data obtained using the electrodes can be transmitted to an EMG recording device that is remote from the subject.

Local and remote uEMG measurements and the transfer of resulting data can be performed using art-known equipment and procedures. Equipment that may be used for data transfer in methods of the invention may include but is not limited to telephones, telephone lines, wireless connections, Ethernet connections, internet connections, computers, mobile devices, smartphones, two-way radios, transmitters, hard drives, memory sticks, flash drives, dedicated transmission, dedicated storage devices, etc.

Devices suitable for use in methods of the invention for recording EMG values are known in the art and may include, but are not limited to multichannel EMG recorders. EMG data obtained from a subject can be transferred to a local or a remote device for data processing, which may include but is not limited to, signal filtering, manipulation, (e.g., data subtraction, formula applications, etc.), data interpretation, graphing, charting, storage, analog to digital conversion, Fourier transform, wavelet analysis, high and low pass filtering, frequency analysis, vector analysis, wave propagation analysis, long term storage, etc.

EXAMPLES

Example 1

Introduction

Mechanical stimulation causes contraction of most smooth muscle types, including myometrium, (Csapo A I. *Prostaglandins* 1977; 13(5):965-973) yet little is known about the role mechanotransduction plays in myometrial contractility. The work outlined below investigated the role of mechanotransduction on coordinating the phasic contractions of myometrium. More than 40 years ago, Csapo proposed that a high degree of organ-level in-phase coordination is required to generate the large intrauterine pressures necessary for cervical dilation in human labor, (Csapo A I, & Takeda H., *Am J Obstet. Gynecol.* 1965; 91:221-231; Csapo A. *Obstet Gynecol Surv.* 1970; 25(6):515-543; and Csapo A., *Obstet Gynecol Surv.* 1970; 25(5):403-435). About the same time, Takeda suggested that contractions of different regions of the rodent uterus can be synchronized using only a mechanotransduction mechanism. (Takeda H. *Fertil Steril.* 1965; 16:113-119). The basis of this hypothesis was that contraction of one part of the uterus mechanically stimulates and induces a contraction in another region. However, these concepts eventually fell out of favor and research focused on electrical signaling as the dominant mechanism for both short- and long-distance communication. (Sigger J N, et al., *J Reprod Fertil.* 1984; 70(1):103-114; and Miller S M, et al., *Am J Physiol.* 1989; 256(1 pt 1):C130-C141).

Example 1 presents studies of interactions of two tissues that are mechanically linked in series, but otherwise isolated in separate baths. A major experimental barrier encountered when studying mechanical properties of linked tissues is that it is difficult to determine whether an observed force is produced by one tissue or the other, or perhaps by both. Previous studies have reproducibly measured tissue-level bioelectrical signals that are closely associated with tissue contractions. (See: Young R C, & Bemis A. *Reprod Sci.* 2009; 16(8):734-739; Young R C, & Zhang P., *J Soc Gynecol Investig.* 2004; 11(7):478-482; Kawarabayashi T, et al., *Gynecol Obstet Investig.* 1988; 25(2):73-79; and Wikland M, & Lindblom B., *Eur J Obstet Gynecol Reprod Biol.* 1985; 20(6):337-346). In rodents, action potential spikes occur in bursts through the duration of the plateau region of the tissue-level action potential. (Chen C J, & Chiang S T, *Proc Natl Sci Counc Repub China B.* 1989; 13(1):42-46). Therefore, by measuring the electrical activity of each tissue, the following studies were able to directly observe when each tissue contracts, precisely determine the duration of each contraction, and directly compare the timing of the contractions of two tissue strips.

The generally accepted mechanism for global uterine coordination is propagation of electrical activity. Mechanotransduction mechanisms were briefly considered as a secondary mechanism 40 years ago, but scant data have appeared. Here, evidence is provided that tissue strips are capable of functionally interacting solely by mechanical mechanisms. Two rat myometrial strips of similar size were mechanically linked in series. Strips were placed in separate baths to ensure they were electrically and chemically isolated. A force transducer was used to measure force production. It was precisely determined when each tissue contracted by simultaneously measuring each strip's electrical activity using contact electrodes. Both in-phase and out-of-phase contraction patterns were observed from the tissues. To determine whether modulation of the electrical properties of the tissue is involved in the mechanotransduction mechanism, the single tissue strips were briefly stretched during alternate contractions. This technique provided a control contraction for each test contraction. The duration of the contraction that was stretched measured longer than the control in 33 of 35 pairs (P=0.0001, Wilcoxon signed-rank test for paired data). Briefly slackening the tissue also prolonged the force-producing phase of that contraction (39 of 42 pairs; P=0.0006). The resulting data showed that mechanotransduction mechanisms coordinate tissue-level contractions, suggesting that mechanotransduction mechanisms may contribute to organ-level coordination of contractions.

Materials and Methods

Timed pregnant rats were purchased from Charles River (Wilmington, Mass.) and used between 20 and 21 days of gestation. Under the University of Vermont IACUC protocol #07-055AP, rats were euthanized using pentobarbital and decapitation and myometrial tissue harvested. Full thickness strips approximately 1.5-mm wide from the antimesenteric side of the uterus were cut parallel to the longitudinal muscle.

Single-Strip Isometric Contractility

Single myometrial strips 1 to 2 cm long (stretched length) were mounted horizontally in an isometric bath as previously described. (Young R C, & Zhang P., *J Soc Gynecol Investig.* 2004; 11(7):478-482). Other than application of a baseline tension of 100 to 250 mg (1 to 2.5 mN), tissues were unstimulated and contractions were spontaneous. The experiment was enclosed in a Faraday cage on a vibration isolation table. The bathing solution was based on phosphate buffered saline solution and contained (in mmol/L) 137 NaCl, 2.7 KCl, 10 $NaH_2PO_4/Na_2HPO_4$, 0.9 $CaCl_2$, pH7.4. Bathing solution temperature was monitored directly using a thermocouple and maintained at 37±1° C. using a DC heating element beneath the chamber. Forces were measured with a Grass Technologies (WestWarwick, R.I.) FT-03 transducer mounted on a micrometer drive. Tension or force was reported in g (where 1 g=10 mN).

A contact electrode was placed from above onto the longitudinal muscle of the tissue. Electrodes were made from 0.7 mm ID glass capillaries containing silver chloride-coated silver wires. Signals were amplified in the AC mode using 2 A-M Systems, Inc (Carlsborg, Wash.) Model 3000 amplifiers. High-impedance probes were used to monitor electrical signals. High-pass filters were set at 1 Hz and low-pass set at 1 kHz. A 60-Hz notch filter was also used to reduce line current noise. Signals were digitized at 10 kHz using AD Instruments (Colorado Springs, Colo.) analog to digital converter PowerLab 8/30. Digitized signals were stored on a personal computer and analyzed using AD Instruments (Colorado Springs, Colo.) Chart 5 software. The tension transducer was mounted on an electrically controlled motorized micrometer drive [Newport Corp., model 860 (North Billerica, Mass.)]. Using this drive, the tissue was stretched or slackened at 0.34 mm/sec.

Two-Strip Isometric Contractility

Two similar-sized strips from the same uterine horn of the same animal were tied end-to-end and mounted horizontally in a dual isometric bath chamber (FIG. 1). The dual chamber was specifically designed to maximize efficient mechanical linkage between the strips, yet fully electrically and metabolically isolate the strips from one another. Bath compartments were separated by 3 mm, and a rigid acrylic plastic bridge was used to transmit forces across the separation. The weight of the bridge was supported by a 25-cm suture, which essentially created a pendulum. Measured resistance between the baths was >100 Mohm. Each bath contained its own ground, and bioelectrical signals were independently recorded from each tissue by monitoring contact electrode signals with separate AC amplifiers. Because the strips were linked end-to-end, the force transducer recorded the forces developed by either strip.

Bioelectrical Data Analysis

Burst durations were measured as the time between the first and last spikes of each burst. Spike rates were calculated using Chart 5 software as follows: Data were filtered using low-pass filter at 50 Hz to reduce detection of spurious peaks. Limits of detections were set to correlate detected unit events with unfiltered, actual spike events. Because event detection was assigned to complex bioelectrical signals, the time resolution was approximated to be half the data filter rate or 25 Hz (40 milliseconds).

Results

Bioelectrical Signals and Force Production

Figure 2:
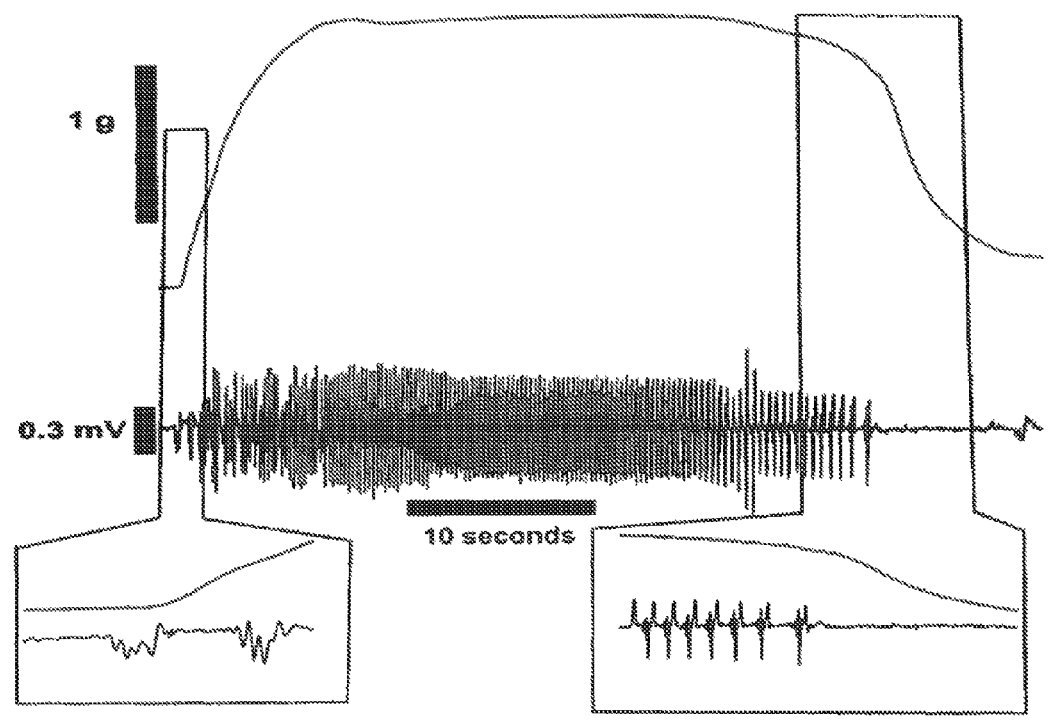
FIG. 2 shows recordings of force and bioelectrical signals from one tissue. Bioelectrical activity occurred in bursts, which were typically composed of 20 to 80 repetitive spikes. As measured with extracellular contact electrodes, spikes are complexes that reflect the summation of electrical activities of the cells beneath the electrode. Burst activity was closely associated with the onset and offset of the force-producing phase of each contraction (insets).

Rat myometrial strips generate bursts of action potentials that are closely associated with force generation, as previously reported. (Young R C, & Zhang P., *J Soc Gynecol Investig.* 2004; 11(7):478-482). FIG. 2 demonstrates the typical force and bioelectrical activities recorded from 1 tissue strip. Bursts without an associated contraction were not observed, although contractions were occasionally observed without a measurable bioelectrical signal. The latter outcome was attributed to be most consistent with inadvertent placement of the electrode over an area of the tissue where the myocytes were not electrically active and contracting.

As seen in FIG. 2, force production began with the first spike of the burst, and relaxation of the tissue began soon after the last spike. These observations were consistent with the known close association of spiking action potentials and rat myometrial contractility. For the remainder of this work, the duration of the force-producing phase of the contraction was approximated by measuring the duration of the burst associated with each contraction of each tissue.

The 2-Strip Experiment

Figure 3:
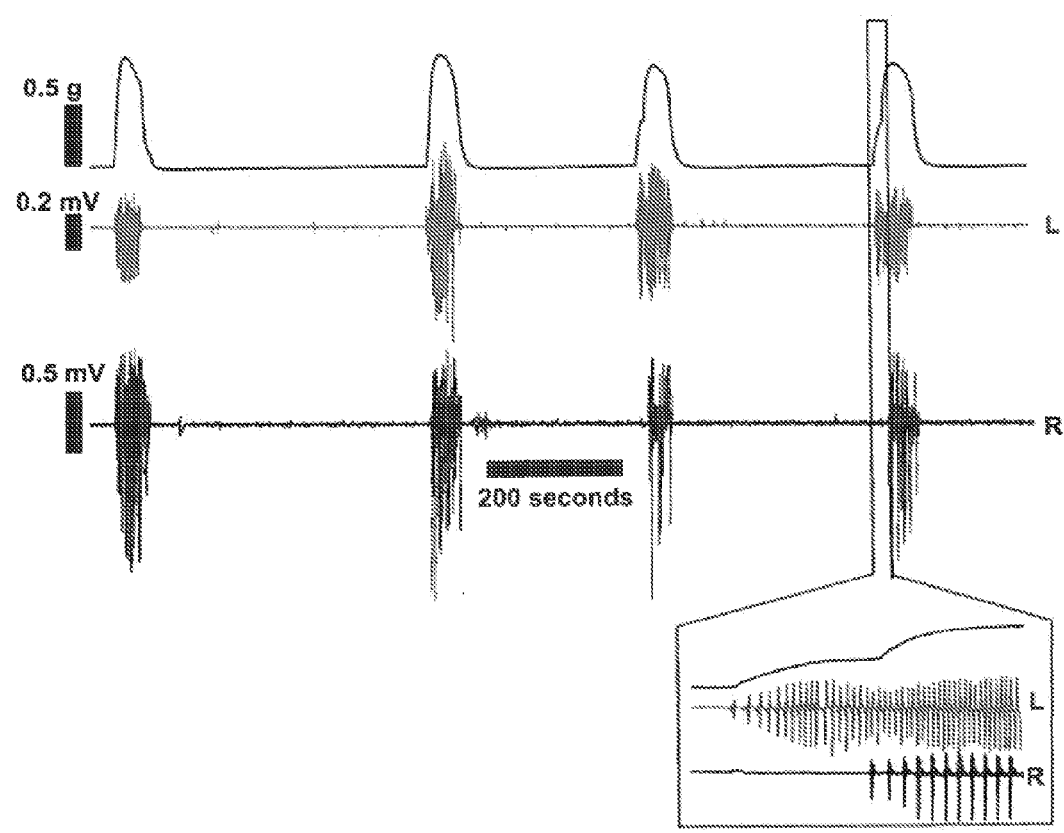
FIG. 3 shows recording traces of synchronized (in-phase coordination) contractions of two tissue strips. L and R are the bioelectrical signals from the left and right tissue strips, respectively. The force curve demonstrates regularly occurring, monophasic contractions. Bursts from each tissue occur at approximately the same time, although close inspection reveals the bioelectrical activities of the two tissues (inset) start and stop at slightly different times. Synchronized contractions are an example of true labor.

In the 2-strip experiment, two electrodes were used—1 for each tissue. If either tissue failed to contract, or bioelectrical signals were not observed from both electrodes, then the experiment was considered unsuccessful. In 35 experimental attempts (i.e., 35 pairs), 16 were unsuccessful; 19 expressed phasic forces with bioelectrical signals recorded from both electrodes. In 6 of the 19 successful experiments, a regularly recurring force pattern (FIG. 3) was observed with highly overlapping burst activity that persisted for at least 6 sequential contractions. Over these intervals of in-phase coupling, neither tissue expressed a burst without the other tissue simultaneously expressing a burst. Close inspection of the spikes within the bursts shows that the bioelectrical activities of the two tissues were not identical (inset)—there were slight differences of start and stop times, and the frequencies of the spike generation within the bursts were not identical. These differences in spike activity confirmed that the two tissues were electrically independent and indicated that direct electrical communication did not occur between the two electrodes.

The high degree of overlap of the burst activities suggested that the tissues contracted in synchrony in these experiments. To determine that this synchrony was not accidental, the probability of the 2 electrodes randomly bursting together was compared against the observed fraction of time that simultaneous bursting was recorded. For each electrode, the probability of bursting over that interval was measured by dividing the sum of the burst durations by the total time of the interval. The two electrodes burst probabilities were then multiplied with each other to obtain the probability that both tissues burst together by chance. The "observed" fraction of time the electrodes were simultaneously bursting was then calculated by measuring the time the electrodes were simultaneously active and dividing by total time of the interval. In the 6 experiments that visually demonstrated synchronized contractions, the overlap of signals averaged 263% that of the chance alone. Using the 2-tailed paired t test, the observed and random probabilities were significantly different (P=0.0002). Thus, the synchronized timing of the contractions of the 2 tissues did not appear to be related by chance alone.

Figure 4:
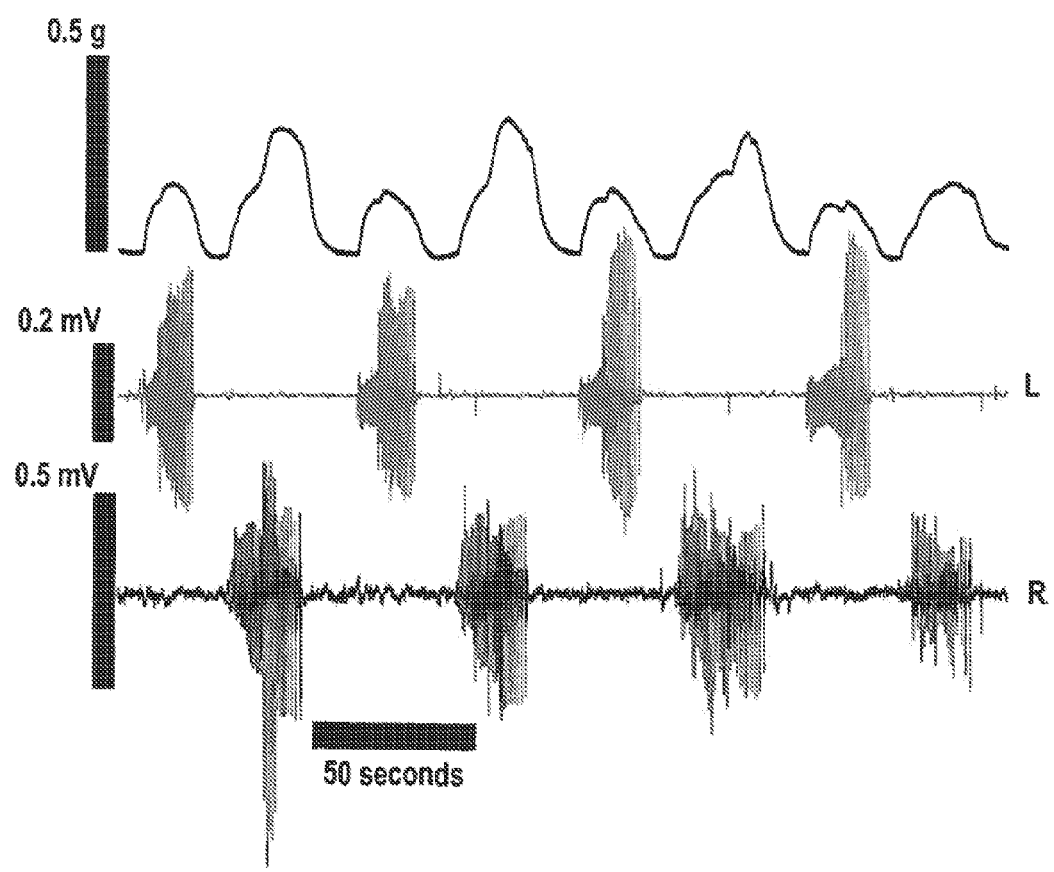
FIG. 4 shows recording traces of out-of-phase coordination of two tissue strips. Forces were observed associated with each burst, but there was no overlap of the bursts of the two tissues. These two tissues display an example of contractions that will not generate large intrauterine pressures and is an example of false labor. Thus, comparing FIGS. 3 and 4, it is shown that mechanotransduction signaling alone can lead to true labor or false labor, and the difference between the two is based on synchronization of the contractions.

Of the 19 successful experiments, 3 generated patterns where the bursts from the two tissues never occurred at the same time (FIG. 4). In each of these cases, the observed probability was 0. Using the 2-tailed paired t test as above, it was found P=0.03, again suggesting this out-of-phase contraction pattern did not occur by chance alone. Taken together, the analysis of the contractions expressed by electrically and chemically isolated, but mechanically linked tissues, indicated that mechanotransduction alone is capable of coordinating myometrial contractions into both in phase and out-of-phase patterns.

Rapid Stretch-Return

The above experiments demonstrate that myometrial tissues functionally interact with each other using mechanotransduction as the only mechanism of communication. Experiments specifically designed to determine myometrial responses to controlled tissue deformation were then performed. These experiments were performed on single tissue strips and tension was modulated with a motorized micrometer drive. To precisely determine contraction durations, contact electrodes were used to measure the duration of the burst activities. Burst durations were calculated from the time between the first and last spikes of each contraction.

Figure 5:
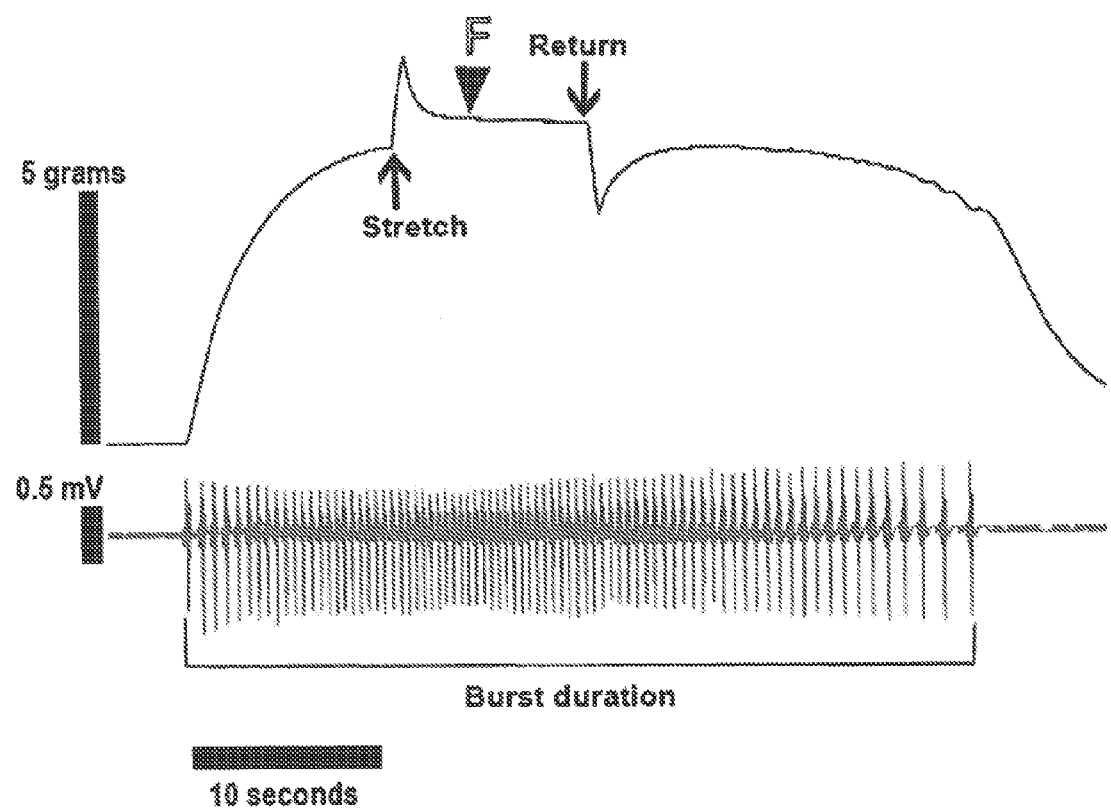
FIG. 5 shows recording tracts from a stretch/return experimental protocol. Length changes are where indicated. Tissue stretch over approximately 1 second results in a rapid increase of tension. After the stretch is completed, the tension rapidly falls, consistent with viscoelastic creep of myometrium. Force (F) is measured at the conclusion of the creep. Recovery of the creep is observed immediately after the tissue is returned to its original length. Burst duration is the time between the first and last spikes.

For approximately 1.5-mm wide tissue strips, typical peak forces were 1 to 5 g (10 to 50 mN). After establishing a baseline contraction pattern, the strip in FIG. 5 was rapidly stretched (0.34 mm/sec) near the peak of the contraction until tension was increased by 1 to 1.5 g (10 to 15 mN). At the conclusion of the stretch, the force rapidly decreased due to viscoelastic creep of the tissue. After 7 to 10 seconds, the strip was returned to its original length and recovery of the viscoelastic creep was observed. (This was called the "stretch-return" experiment.) Stretches were performed on every other contraction so that one control contraction occurred for each stretch-modulated contraction.

Six stretch-return experiments were performed. Each experiment contained at least five pairs of control and stretch-return (test) contractions. Each stretch-return contraction was compared with the control contraction that immediately preceded it. In 35 contraction pairs analyzed, 33 showed that the duration of the burst activity of the test contraction was longer than its control, and 2 were less than its control. Because a normal distribution for burst durations can't be assumed, the 2-tailed Wilcoxon test for paired data was used to determine the significance of the differences between burst activities and found P=0.0001. Because the burst duration is associated with the duration of force production, these data indicate that acutely stretching rat myometrium through the force-producing phase of a contraction increases the duration of the contraction.

The peak forces of the stretch-return contractions were compared with controls using the 2-tailed Wilcoxon test for paired data. Peak forces were measured at the completion of the viscoelastic creep after the stretch. The results indicated that 33 of 35 peak forces were increased when the tissue was stretched (P=0.0001). Thus, both force duration and peak force were found to be increased by transient stretch of the tissue. Both of these results could have resulted from changes along the length-tension relationship of the tissue and not because of mechanical transduction effects on the tissue. To assess this possibility, the effects of acutely slackening the myometrium were investigated.

Rapid Slack-Return Experiments

Figure 6:
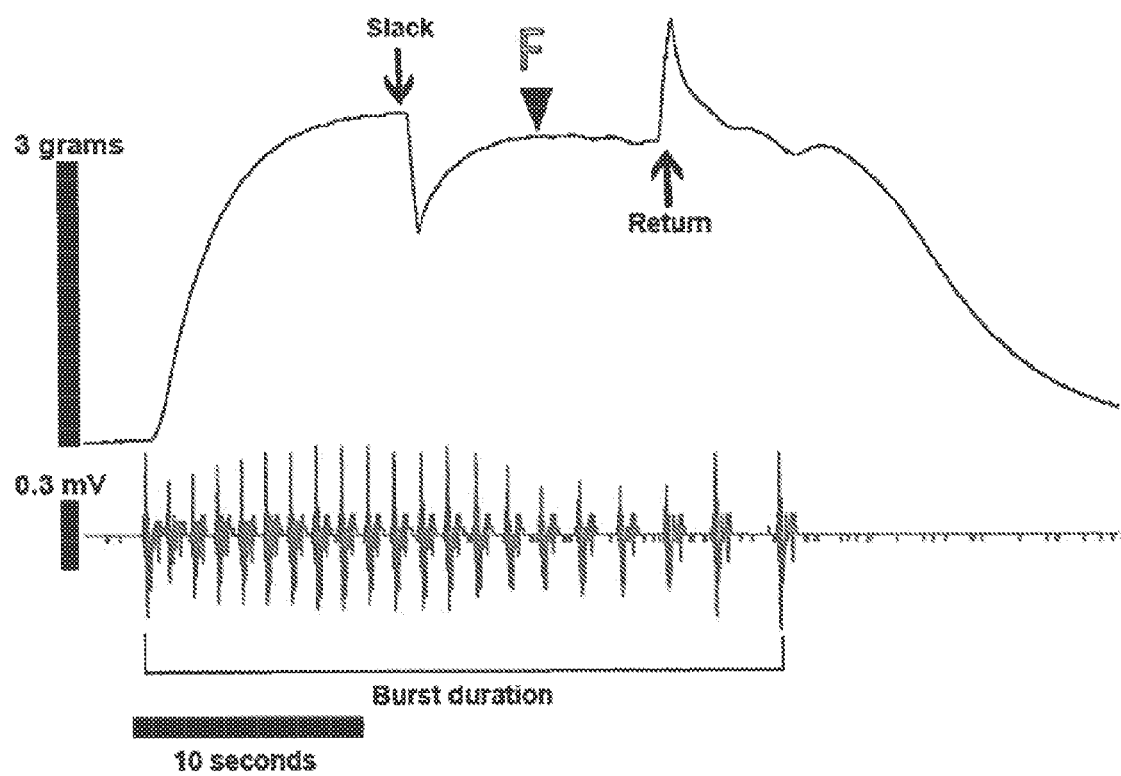
FIG. 6 shows recording traces from a slack/return experimental protocol. The protocol is analogous to that shown in FIG. 5 expect the initial tissue deformation is slackening.

Slack-return experiments (FIG. 6) were performed in an analogous manner to the stretch-return experiments. Six slack-return experiments expressing 42 pairs of control and test contractions were analyzed. Two pairs showed no difference of the burst durations within limits of measurement error (40 milliseconds). For 1 pair, the control contraction was longer. The remaining 39 pairs showed longer burst durations with the test contraction (P=0.0006, Wilcoxon 2-tailed test for paired data). Therefore, these data indicate that slackening myometrium also, somewhat surprisingly, increases the duration of force production.

Peak forces were measured after slackening of the tissue, similarly to the measurements taken after stretching in the stretch-return experiments. For the 42 pairs of contractions, 7 were greater than the control, but the remaining 35 showed a peak force less than control (P=0.001, 2-tailed Wilcoxon test for paired data).

Because peak forces were increased following a stretching of the tissue, but decreased following slackening of the tissue, these results were interpreted as indicating that peak forces are more dependent upon the length-tension relationship of the tissue than on tissue deformation. The finding that both stretching and slackening of the tissues resulted in lengthening of the burst durations indicated that contractions last longer when tension changes in either direction.

Discussion

The two-tissue experiments were performed using separate baths for each tissue to eliminate the possibility of electrical or chemical signaling between the two tissues. In FIGS. 1 and 2, it is clear that without the bioelectrical data from each tissue, it would not be possible to determine whether one or both tissues were contributing to the observed force at a given time. It is also important to note that the tissues were purposefully cut to approximately the same cross-sectional areas to reduce the possibility that one tissue mechanically overwhelmed the other. These experiments clearly demonstrated the coordinating effects of mechanotransduction as the sole signaling mechanism.

The majority of the successful experiments (10 of 19) demonstrated patterns where the two tissues either contracted independently or changed between in- and out-of-phase patterns after a few contractions. In-phase mechanical synchronization was observed in only 6 of 19 experiments and out-of-phase synchronization in only 3 of 19. This relatively small percentage is perhaps not surprising, because the intact uterus spends the vast majority of time in a quiescent state to allow for fetal development.

The most reasonable mechanism for mechanical synchronization of contractions of two linked tissues involves one tissue beginning a contraction and generating a force that pulls on the second tissue. This pull, or tension change, then may rapidly initiate a contraction in the second tissue, and both tissues would be observed to contract simultaneously. One mechanism to initiate a contraction is through tissue depolarization. To test the ability of mechanical deformation to modulate the electrical properties of the tissue, an experiment was performed that directly measured the burst duration of strips subjected to a transient stretch during the force-producing phase of the contraction.

These single-strip experiments showed that either slackening or lengthening the tissue resulted in prolongation of the burst duration. This observation directly indicated that the duration of the plateau of the tissue-level action potential is prolonged by mechanical deformation, and specifically implies mechanical deformation modulates the electrical properties of the tissue. Any process that involves either activation of depolarizing currents or inhibition of repolarizing currents could cause plateau potential prolongation. Further mechanical studies on single cells are performed to further elucidate these mechanisms.

Alternately, it is possible that coordination of contractions in the two-tissue experiment is via a phase-locking mechanism that directly depends on modulation of contraction duration. In- or out-of-phase locking may result from a temporal overlap of each tissue's refractory or excitable periods. In this formulation, it is necessary to assume that each tissue has an inherent contraction frequency, and these frequencies become phase locked by variations of the contraction duration.

Mechanotransduction has been well-studied in vascular smooth muscle and is the underlying mechanism of the vascular myogenic response. (Osol G. et al., *Am J Physiol.* 2002; 283(6): H2260-H2267). The vascular myogenic response is physiologically important because it is known to assist with maintenance of tissue blood flow in the presence of changing blood pressure. Interestingly, the vascular myogenic response is not observed in nonpregnant mouse uterine arteries but is active in these arteries in pregnancy. (Veerareddy S. et al., *Am J. Physiol.* 2002; 283(6):H2226-H2233). The current results in myometrium provided herein suggest mechanotransduction maybe the underlying mechanism in what may be considered an analogous myometrial myogenic response. Although the vascular myogenic response is tonic, the results suggested that the myometrial myogenic response is the phase coordination of contractions of mechanically coupled myometrium. Increased contractility following length changes of human myometrium has been reported by Hurd et al. (Hurd W W. et al., *Am J Obstet Gynecol.* 2005; 192(4): 1295-1301; and Hurd W W, et al., *Am J Obstet. Gynecol.* 2008; 198(2):225 e1-225 e4). In the experiments provided herein, the tissues were slackened only while force was being produced, then returned the tissue to its previous length before the contraction was completed. Hurd acutely changed tissue length but did not return it to its starting length. In addition, the in the work described herein a separate analysis was performed on the peak force and the contraction duration.

Clinically, rises of intrauterine pressure define labor, (Hauth J C. et al., *Obstet. Gynecol.* 1986; 68(3):305-309) and as previously pointed out by Csapo, (Csapo A., *Obstet Gynecol Surv.* 1970; 25(6):515-543) intrauterine pressure and uterine wall tension are related by Laplace's Law. (Csapo A I, & Takeda H. *Am J Obstet. Gynecol.* 1965; 91:221-231; Csapo A., *Obstet Gynecol Surv.* 1970; 25(6):515-543; Basford J R, *Arch Phys Med. Rehabil.* 2002; 83(8):1165-1170). Takeda (Takeda H. *Fertil Steril.* 1965; 16:113-119) expanded this concept into a unifying organ-level mechanotransduction mechanism he called "hydrodynamic signaling," although "hydraulic pressure-tension signaling" is perhaps a more accurate term. Mechanotransduction mechanisms do not diminish the importance of electrical activity in myometrial contractility, but rather emphasize it. Indeed, the data presented herein are consistent with electrical activity being both necessary and sufficient for force production at the tissue-level. However, the data presented herein also suggest mechanotransduction also contributes to tissue-level coordination of contractions and maybe especially important when signaling is not contiguous or is faster than the action potential propagation rates that myometrium can express.

Example 2

Introduction

This Example addresses organ-level uterine function and the contractions of labor (e.g. contractions that dilate the cervix) versus non-labor (contractions that do not dilate the cervix). It has been identified that contractions of labor are well coordinated at the organ-level.

Results of the studies presented herein indicate that uncoordinated uterine contractions may not raise intrauterine pressure enough to cause cervical dilation. The goal of experiments presented herein is to investigate organ-level coordination of the gravid human uterus and determine if a high degree of coordination is necessary for true labor, and if uncoordinated contractions are associated with false labor.

The results of this work address multiple areas of interest including at least: 1. Being able to identify true labor by non-invasively assessing uterine contractions allows medical management of preterm labor to be started prior to cervical change; 2. Being able to identify false labor reduces unnecessary medical therapies; 3. The ability to inexpensively assess uterine contractions on an ongoing basis directly assists with management of patients at high risk for preterm labor; 4. Information on coordination of uterine contractions leads to improved knowledge of the physiology of labor at the organ-level, and ultimately leads to development of new methods to control uterine contractility.

The well-established technique of uterine electromyography (uEMG) has now been expanded into a novel technique to individually assess the four quadrants of the pregnant uterus (4Q EMG). uEMG is non-invasive and has been proposed as a replacement for clinically accepted tocodynamometer (toco) recordings. Both toco and uEMG accurately record the timing of contractions, and uEMG also has the potential to semi-quantitatively assess the strength of each contraction. To date, uEMG has generally not replaced the toco since a clear benefit of uEMG has not been established for a specific clinical situation.

A previously unexplored advantage of uEMG is the ability to assess temporal activity of different regions of the uterus. Studies outlined herein utilize 4Q EMG to record the timing of the contractile activity of the four quadrants of the pregnant uterus to measure the degree of organ-level coordination. This information is clinically relevant for assessment of true labor. The tests described herein that utilize the uEMG quadrant technique are inexpensive to perform, do not overly restrict patient movement, and provide enough information to clinically assess organ-level coordination of uterine contractions.

Test Protocol 1

Electrode placement is optimized to simultaneously record from 4 quadrants of the uterus, and software is prepared that concisely, and without bias, summarizes the degree of synchronization of activity in the quadrants. Pregnant women near term who are experiencing contractions are studied. The location of the 4 pairs of electrodes on each woman is adjusted to minimize uEMG cross-talk and maximize signals. To concisely describe the degree of synchronization of the four channels, a "synchronization factor" (SF=sum of signal duration of all 4 electrodes/4×signal duration of the contraction) is used. The value of SF varies between ~0 (unsynchronized) and 1.0 (fully synchronized) for each contraction. Using probability equations, SF is combined with the frequency of contractions and the relative strength of contractions to create a composite "Labor Status" variable.

Test Protocol 2

A study is performed to test the ability of the Labor Status to predict delivery within 24 hours. SF is measured using 4Q EMG on the contractions of term and late preterm pregnant women in true and false labor, and Labor Status is calculated. The probability calculation of Labor Status sensitivity and specificity are optimized for diagnosis of true labor. Methods are used that allow a reasonable positive predictive value, allowing diagnosis of preterm labor before cervical dilation occurs.

To clinically measure the degree of uterine contraction coordination, measurements of the regional activity of the uterus are made using electrodes such as surface electrodes. Uterine electromyograph (uEMG) is used to determine if all regions of the uterus are simultaneously active. The 4 quadrants of the uterus are assessed and the technique is referred to as 4Q EMG.

Subjects studied are ≥36 weeks pregnant. Earlier preterm patients who are contracting often require rapid implementation of clinical interventions. Additional tests of women in earlier preterm labor are also performed.

Contractions of a critical frequency and strength are required for true labor. A third requirement—organ-level coordination of many regions has now been identified. Results support a mechanism of action potential propagation for coordination within a region, and tension-activated contractions for organ-level coordination of the regions and data suggest indicate that a high degree of synchronization of many regions of the uterus is necessary for true labor.

These studies indicate that the measure a third factor of labor—the synchronization of the regional contractions of the uterus—when combined with contraction frequency and strength measurements can be used to accurately predict both true and false labor. To assess organ-level synchronization a novel arrangement of four uEMGs is utilized to independently probe the contraction status of each quadrant of the uterus. A novel synchronization factor (SF) is used that concisely summarizes the degree of organ-level synchronization, thereby making the information clinically useful. The three factors (frequency, strength, and synchronization) are combined to create an overall assessment of the Labor Status of the whole uterus. The Labor Status is coordinated with the delivery outcome demonstrating the sensitivity and specificity for use of these three factors to determine true labor and assess labor status.

Organ-level synchronization is a third factor necessary for true labor. The measurement of organ-level synchronization is optimized and results analyzed. Placement of 4 uEMG electrodes is optimized to independently measure 4-quadrant activity, with a goal of maximizing signals while minimizing cross-talk between electrodes.

EMG electrodes function by measuring slight differences of AC potentials. These potentials are the expression of small currents that are generated by the voltage changes of the electrically active tissues. The current pathways are dependent upon the tissue conductances. Because the currents fall logarithmically as the distance traveled increases, the direct pathway between each pair of electrodes is a good approximation of the activity of the tissue directly between the electrodes. As exemplified by the standard (cardiac) EKG, it is possible to probe specific regions of electrically active tissue by judicious placement of skin electrode leads.

The heart analogy differs significantly from the uterus in that the heart has specific conduction pathways, which are not present in the uterus. For the uterus, the presence or absence of signal is determined.

Figure 7:
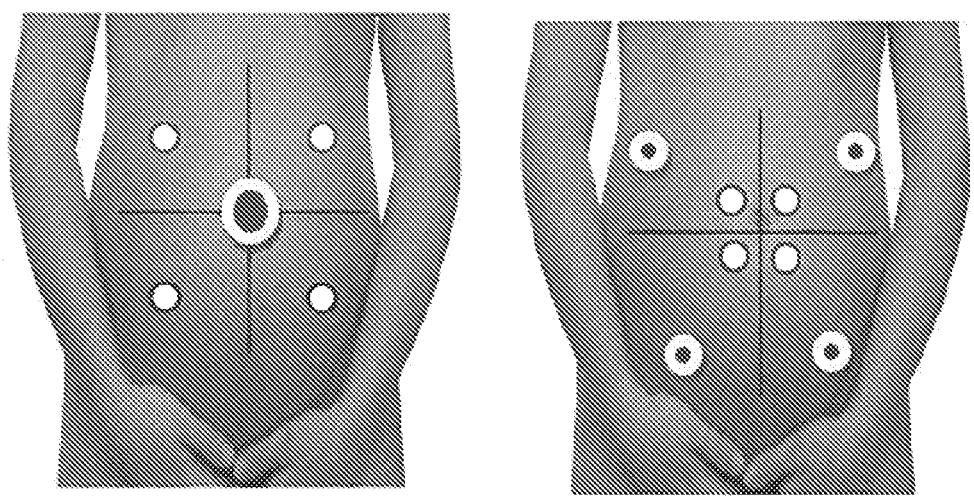
FIG. 7 shows photographic images of examples of positioning of recording electrodes on the abdomen of a pregnant woman.

In one test, a common ground is placed near the umbilicus—centrally on the abdomen. The "active" electrodes are then placed at the outer extremes of the patient's anterior abdominal wall (FIG. 7a). This arrangement has the advantage of ease of use, but may introduce cross-talk among the electrodes. In a second test, four pairs of electrodes are oriented so that the electrodes are vectored away from the other pairs, thereby independently probing each quadrant (FIG. 7b).

Test 1
Methods:
Pregnant women between gestational ages 36 and 41 weeks are tested, including three patients clinically thought to be in labor, and three patients believed to be not-in-labor (but experiencing contractions). Skin EMG electrodes are placed on the patients using one of the physical arrangements described above. Fifteen minutes of 4Q EMG is recorded for each patient, while marking when the patient experiences the onset, peak and offset of each contraction. The other electrode arrangement is then used on the same patient to an additional 15 minutes. The signals obtained from each electrode pair are compared obtained and the arrangement that generates the largest signal with the least cross-talk is identified. Additional electrode orientations and spacing are also tested to identify arrangements yielding separable signals. These tests also provides preliminary data for calculation of SF (Test 2 below herein).

Results

Figure 8:
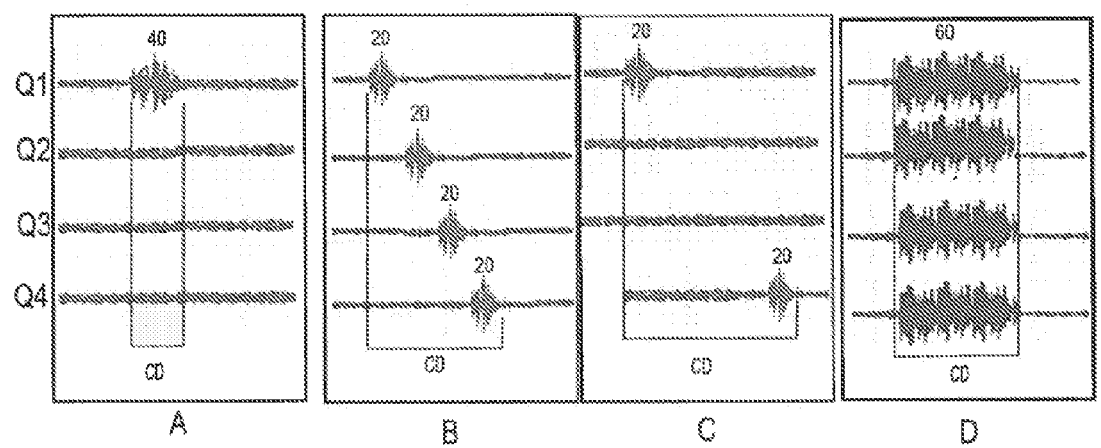
FIG. 8 shows exemplary EMG recording tracings from a pregnant subject.

Both electrode configurations allow recording of uEMG signals of sufficient amplitude, and the configuration with the least cross-talk is selected for further development. The SF (Synchronization Factor of the 4Q EMG) is calculated and concisely summarizes the degree of synchronization of signals from the four electrode pairs. Both synchronized and unsynchronized signals are observed and method permits the quick, concise, and without bias, assessment of the degree of synchronization of the electrode pairs. FIG. 8A-C shows three examples of unsynchronized signals, and FIG. 8D shows an example of a fully synchronized contraction. For A-C, the four electrodes essentially do not demonstrate activity at the same time, but in D all electrodes show active signal at some time. The synchronization factor (SF) is calculated as the sum of the duration of the signals from each channel, divided by four times the contraction duration (CD: time between the first signal and the last; * is "multiplied by").

| | | | |
|---|---|---|---|
| For A: | SF = (40 + 0 + 0 + 0)/4* 40 = | 0.25 | Poorly synchronized |
| For B: | SF = (20 + 20 + 20 + 20)/4* 80 = | 0.25 | Poorly synchronized |
| For C: | SF = (20 + 0 + 0 + 20)/4*80 = | 0.125 | Poorly synchronized |
| For D | SF = (60 + 60 + 60 + 60)/4*60 = | 1.0 | Maximally synchronized |

Hence, SF varies between ~0 and 1.0, and depends directly on the presence of signal from all electrodes and in the amount of overlap of the four signals—the degree of synchronization. To create a composite predictor, all three parameters of labor are used to calculate the "Labor Status".

Boolean algebra is used to calculate the Labor Status, and the calculations are extended to include the Boolean unit interval [0,1] as is used for probability theory. Here, instead of the usual no or yes, the individual values can vary between 0 and 1. In this type Boolean algebra the operations are the same, although they are calculated differently in practice: a AND b is replaced by a*b; a NOT b becomes b-a. Additionally, it is easy to reduce weight of a variable by not using the full range of values between 0 and 1.

Contractions are characterized by f (frequency–Cx/hr), s (strength), and SF (Cx=contraction). For one example, all 3 parameters are necessary but not sufficient, and carry equal weight.

Labor Status=f multiplied by s multiplied by SF    Equation 1

For these examples the following look-up table is used:

TABLE 3

Exemplary values for labor status calculation

| f (Cx/hour) | s (strength) | SF (synchronization factor) |
|---|---|---|
| 0 → 0 | weak → 0 | (range is 0 to 1, |
| 1 → .1 | mild → .2 | the measured value) |
| 2 → .2 | moderate → .6 | |
| 3 → .3 | strong → 1 | |
| 4 → .4 | | |
| 5 → .5 | | |
| 6 → .6 | | |
| 7 → .7 | | |
| 8 → .8 | | |

TABLE 3-continued

Exemplary values for labor status calculation

| f (Cx/hour) | s (strength) | SF (synchronization factor) |
|---|---|---|
| 9 → .9 | | |
| 10 → 1.0 | | |

Example A. 15 minutes elapse since the prior contraction (4 Cx/hr; f=0.4), strength is moderate (s=0.6), and SF is measured to be 0.5.

Labor Status=0.4*0.6*0.5=0.12, suggesting the patient is not in labor.

Example B. 6 minutes elapse since prior contraction (10 Cx/hr; f=1), strong contractions (s=1), SF is 0.9

Labor Status=1*1*0.9=0.9, suggesting the patient is in labor

Additional richness to the Labor Status is also attained using a more detailed equation. For example, if the frequency is >4 Cx/hr there is no dependence on further increases. Hence, instead of equation 1, the following is used:

Labor Status =IF (f>0.4) THEN (Labor Status=s multiplied by SF)

The 4Q EMG is measured in five patients in true labor (as defined by documented cervical change), and five patients who present for repeat Cesarean delivery who are experiencing painless contractions (and have not changed their cervical exam). From these tracings the SF is calculated from at least three contractions per patient. The frequency and strength of each contraction is assessed and the Labor Status is calculated as described above herein.

The SF from laboring patients is >0.75 and SF from non-laboring patients is <0.5. These initial values are selected since SF=0.75 indicates that on average 3 of the 4 quadrants are simultaneously active (e.g. favors labor), and <0.5 indicates less than 2 of the 4 are synchronized.

The Labor Status ranges between 0 (suggests not-in-labor) and 1.0 (suggests labor), due to variations in any of the three parameters. From the average values of the 5 patients in each group a threshold for Labor Status is selected, separating in labor from not-in-labor, which is used as a starting point in Test 2, below herein.

Contraction-to-contraction variability of Labor Status occurs and sequential contractions yield different values. For this reason, the "running average" Labor Status is also calculated. This secondary variable correlates with cervical dilation and true labor, and is also be studied in detail in Test 2 below herein. Software is used to calculate SF and Labor Status (for each contraction, and the average) in real time. Individual Labor Status values are plotted as a function of time to summarize dynamic changes.

Test 2: A Study to Test the Ability of the Labor Status to Predict Delivery within 24 Hours.

Methods and Results

Frequency, strength and synchronization factor (SF) of uterine muscle contractions are measured, and the Labor Status of pregnant women experiencing contractions is calculated. Each patient is followed for 24 hours to determine the primary outcome (if she delivers or not), and the Labor Status is compared with delivery. A Labor Status threshold value is selected (e.g. from the data obtained in Example 2, Test 1 herein); the sensitivity and specificity of Labor Status for predicting delivery is calculated; and the receiver operating characteristic (ROC) is generated.

Patients are consented for study after presenting to labor and delivery for evaluation of labor, or after presenting to the outpatient clinic for evaluation using the fetal non-stress test (NST). NSTs are fetal testing by monitoring the fetal heart beat and uterine contractions via toco. They are routinely performed in the outpatient setting to assess the health of the fetus in patients with high risk conditions. NSTs last up to 30 minutes and patients often experience contractions every 5 minutes. Most in this patient population are not-in-labor, and most who present to labor and delivery are in labor. In each patient setting, toco readings (which is standard of care) and 4Q EMG are simultaneously measured.

Patients studied are 36 to 41 weeks pregnant. Twenty two patients from each setting are studied, obtaining data from 44 patients, half in labor (see targeted enrollment for study size calculations). All patients have a cervix exam <2 cm (and Bishop's score <5). The frequency, strength, and SF values are obtained and the Labor Status calculated for each patient. In some studies, the method of calculating Labor Status (equation 1) is changed, based on observed outcomes as a function of each variable, assuming total independence. The Labor Status values are compared with the diagnosis of true labor, using 24 hours to delivery as the determiner of whether the patient is in true labor. A ROC is created for each equation, and the equation yielding the optimal sensitivity and specificity is determined. In some tests of Labor Status contraction, strength is estimated using EMG amplitudes to reduce the subjective assessment of the strength factor.

Example 3

Figure 9:
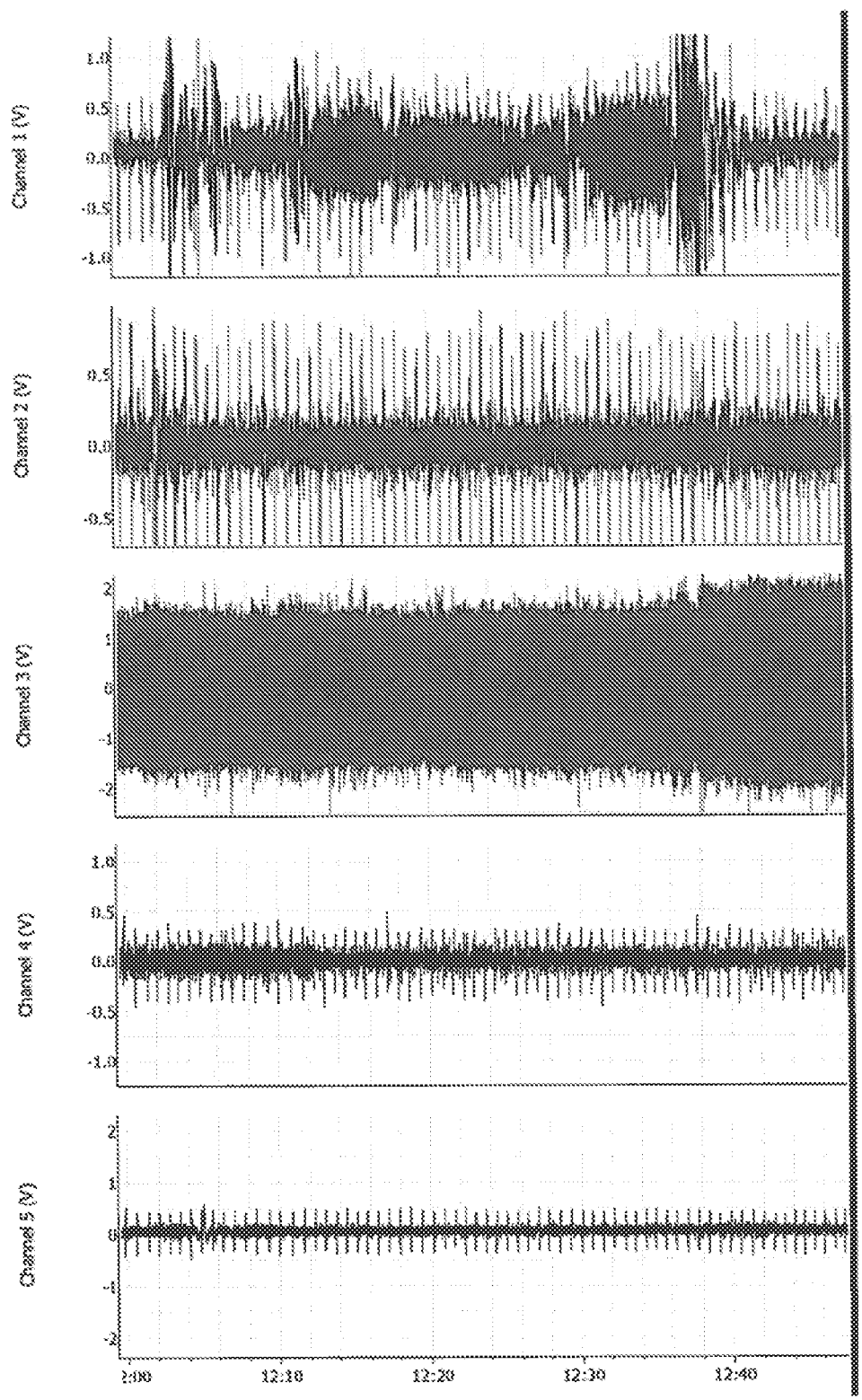
FIG. 9 shows five channels of data, unfiltered, showing fetal heart rate, but without ability to distinguish EMG signals that arise from the uterus.
Figure 10:
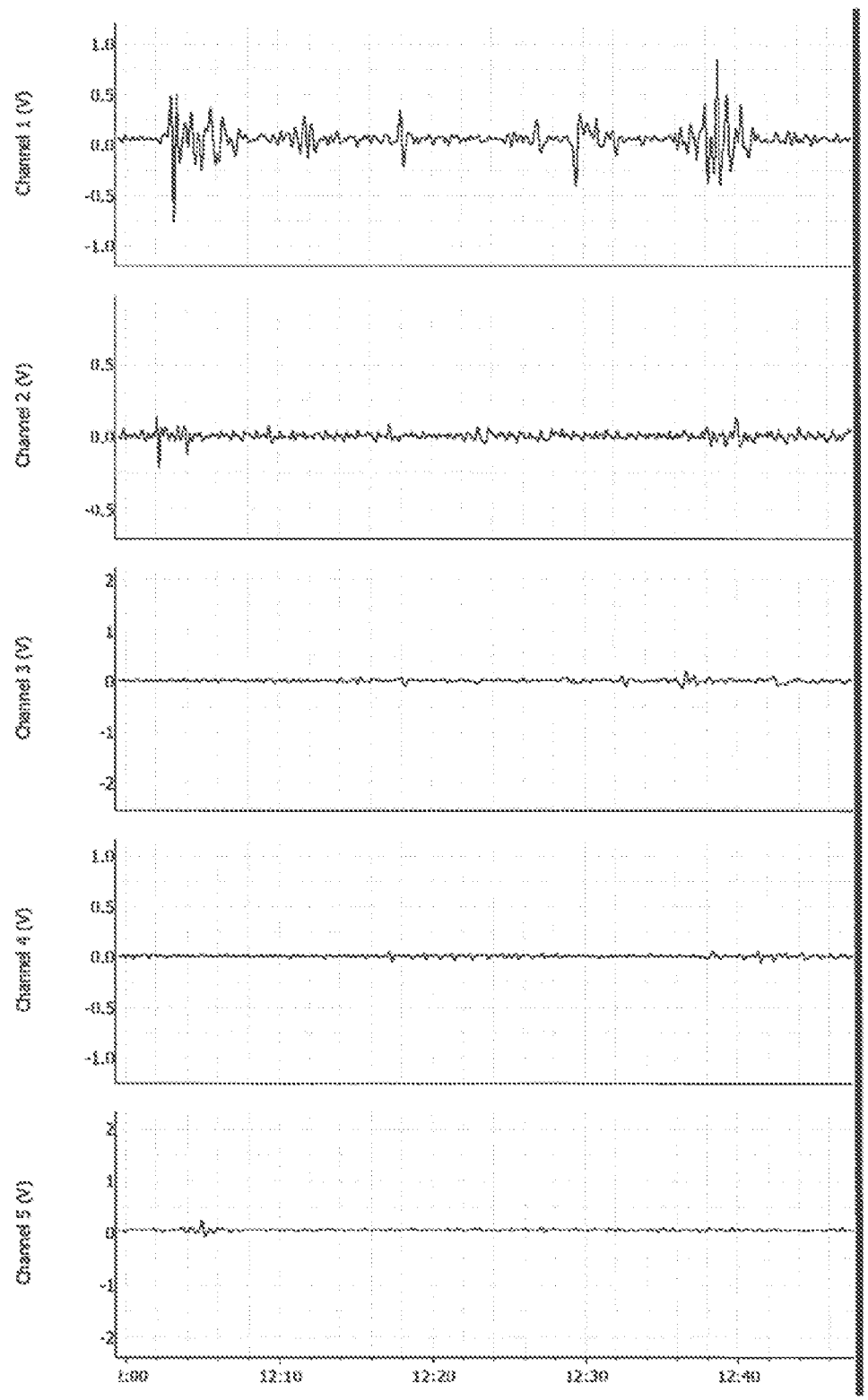
FIG. 10 shows five channels of data (same data set as shown in FIG. 9) after filtering, showing uterine EMG signal in channel 1, but none in channels 1-4, which demonstrates use of the recording methods of the invention to obtain signals from localized sites.
Figure 11:
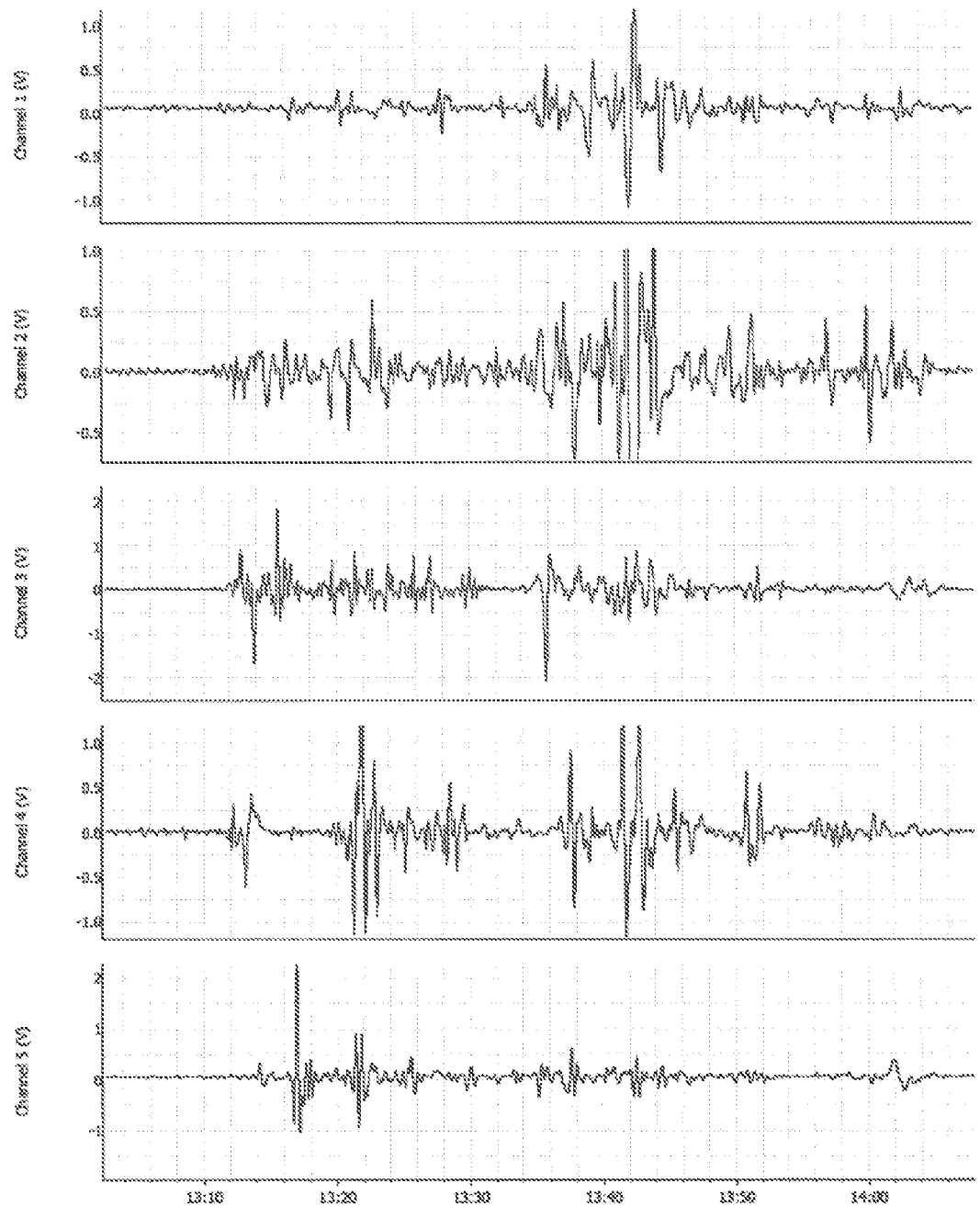
FIG. 11 shows five tracings recorded from the same subject as recorded from in FIGS. 9 and 10 (same electrode positioning) several minutes after the recording data shown in FIGS. 9 and 10 was obtained. The five tracings show the presence of simultaneous signals from all five electrode pairs, indicating synchronous contraction in the five regions of the subject's uterus.

A multichannel EMG recorder (Motion Lab Systems, Los Angeles, Calif.), was used to record 5 channels of EMG data on term pregnant patients. Each channel consisted of a pair of contact pad electrodes that were separated by 4-5 cm. Four pairs of electrode pads were arranged on the patient concentrically around the umbilicus, and one electrode pad was placed centrally just inferior to the umbilicus. The data from the five channels were filtered by low pass and high pass digital filters. As shown in FIG. 9, without data filtering, the fetal heart rate was easily observed, but meaningful signals from the uterus are not discernible. After filtering the data to isolate signals from the uterus, multichannel comparisons showed areas without synchronization (FIG. 10), and areas with synchronization (FIG. 11). This patient was not in labor, and the dominant pattern was without synchronization. These data demonstrated the ability to record regional uterine activity and discriminate between synchronous and asynchronous contractions.

FIG. 9 shows five channels of data, unfiltered, showing fetal heart rate, but without ability to distinguish EMG signals that arise from the uterus. FIG. 10 shows five channels of data (same data set as shown in FIG. 9) after filtering, showing uterine EMG signal in channel 1, but none in channels 1-4. This is an example of regional contractility and demonstrates the ability to obtain signals from localized sites. FIG. 11 shows five tracings recorded from the same subject (same electrodes and positioning) several minutes after the recording data shown in FIGS. 9 and 10 was obtained. The five tracings show the presence of simultaneous signals from all 5 electrode pairs, indicating synchronous contraction in the five regions of the subject's uterus.

Example 4

It has been determined that the number of channels that can be recorded from a pregnant human uterus could be selected based on the electrode contact pad size and the distance between the pads. Electrode contact pads that were about 2.5×2.5 cm in sized were utilized with a distance between the pads of about 4-5 cm. It was determined that the pads of the recording electrodes could each be paired with its own ground electrode, or two or more recording electrodes could be paired with a single ground electrode. It was determined that using electrical data obtained from many electrodes using a common ground position could be recorded, and then signals obtained from two recording electrodes that shared a ground were subtracted to attain the difference of electrical signals between the locations of the two electrodes. This subtractive procedure was repeated using the signals from different recording electrodes that shared a ground electrode. This procedure essentially used the active recording electrode pad of one channel as the ground for another channel, and is possible if each pad is independently isolated. This was possible by using a multi-output operational amplifier for each channel.

Example 5

At least 5 channel resolution using 6 pads (one for ground reference) is obtained, which allows an increase of the number of effective channels for a given number of pads. FIG. 12 shows an example of positioning of recording electrodes over the surface of a pregnant abdomen. This arrangement includes 7 recording electrodes plus one ground electrode, which is shown in FIG. 12 positioned on the subject's abdomen. In some determinations the ground electrode is instead placed on the subject's thigh. With either electrode arrangement, the following regions are assessed: 1 minus 2; 2 minus 3; 3 minus 4; 4 minus 5; 5 minus 6; 6 minus 1, 7 minus 1; 7 minus 2; 7 minus 3; 7 minus 4; 7 minus 5; and 7 minus 6. Thus, a total of 12 regions are assessed with only 7 recording electrodes and one ground electrode. Note that electrode 7 utilizes 6 independent reference outputs, and each of the other channels utilizes 3 independent reference outputs.

Signal processing is performed to isolate regions of uterine activity. Raw data frequency patterns of, for example, the three pairs 1-2, 1-7 and 1-6 are obtained. Dominant signals from the first pair, 1-2, is assessed and stored. The other two pairs, 1-7 and 1-6, are tested for the presence of identical patterns. The signal of 1-2 is individually scaled to match each pair, and then signals are subtracted yielding 1-7 and 1-6 signals corrected for 1-2 region overlap. This is repeated for each pair in turn. At the end of the analysis, corrected signals from all regions, 1-2,2-3, 3-4,4-5, 5-6,6-1, 1-7,2-7, 3-7,4-7, 5-7, 6-7 result. Each signal then represents the signal directly underneath the physical location of each electrode pair. SF is then calculated from corrected signals, and determination of labor status is calculated.

Labor status is determined using SF, frequency of contractions and strength of contractions as described elsewhere herein. Labor status indicates if a patient is in true labor or false labor, and on that basis clinical decisions are made. If a patient is in true labor and is preterm, specific therapies for preterm labor are initiated. Preterm patients who are determined not to be in labor are not treated with potentially harmful medications and may be sent home. Patients at term who are determined to be in true labor are retained in clinical observation with plans for delivery. Patients at term and determined not to be in labor may be sent home. During inductions of labor for other clinical reasons, the SF and labor status are used to assess adequacy of induction to create contractions of labor. Should a low labor status level be determined, one or more labor-enhancing medications or procedures are administered and/or the level of medication administration is increased. Should a high labor status level be determined, the clinical course is maintained. Should excessive, or maximal, labor status be determined, administration of the labor-enhancing medications or treatments are reduced.

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

What is claimed is:

1. A method of determining labor status in a pregnant subject, the method comprising:
   receiving, at an electromyography (EMG) recorder, a plurality of signals, each of the plurality of signals comprising an EMG signal generated by different regions of a subject's uterine wall and measured with a respective one of a plurality of electrode pairs, each of the electrode pairs positioned on the subject's abdomen in a manner minimizing or eliminating overlap of the signal of the plurality of signals measured by two or more of the positioned electrode pairs;
   detecting three or more uterine muscle contractions, each of the three or more detected uterine muscle contractions associated with a respective one of the plurality of signals;
   calculating a synchronization factor of the three or more uterine muscle contractions based on a ratio of a summed duration of each of the three or more detected uterine muscle contractions to a total time spanned by the three or more detected uterine muscle contractions; and identifying, responsive to the synchronization factor crossing a predetermined threshold, a labor status of the subject.

2. The method of claim 1, further comprising comparing the synchronization factor of the three or more uterine muscle contractions to a control regional synchronization pattern.

3. The method of claim 1, wherein the method further comprises:

measuring a strength and a frequency of the three or more uterine muscle contractions; and calculating the synchronization factor responsive to the strength and the frequency of the three or more uterine muscle contractions.

4. The method of claim 1, further comprising positioning each of the plurality of electrode pairs on a surface of the subject's abdomen.

5. The method of claim 1, wherein each of the plurality of electrode pairs comprise a ground electrode and a recording electrode.

6. The method of claim 1, wherein the labor status is absent, latent phase labor, active phase labor, delivery of the baby, or afterbirth-delivery.

7. The method of claim 1, wherein the subject has been, is currently, or will be administered one or more labor-enhancing treatments.

8. The method of claim 1, wherein the subject has been, is currently, or will be administered one or more labor-inhibiting treatments.

9. The method of claim 1, further comprising receiving the plurality of signals from a remote device.

10. The method of claim 1, wherein the labor status is one of true labor and false labor.

11. The method of claim 1, further comprising diagnosing a medical condition in the subject responsive to the labor status.

12. The method of claim 11, wherein the medical condition is false labor.

13. The method of claim 11, wherein the medical condition is premature labor.

14. The method of claim 1, further comprising selecting a treatment for the subject based at least in part on the identified labor status.

* * * * *